US011422131B2

(12) United States Patent
Seckler et al.

(10) Patent No.: US 11,422,131 B2
(45) Date of Patent: Aug. 23, 2022

(54) SENSOR FOR DETECTION OF ANALYTES

(71) Applicant: Case Western Reserve University, Cleveland, OH (US)

(72) Inventors: James M. Seckler, Cleveland, OH (US); Neil A. Goldsmith, Sheffield Village, OH (US); Stephen J. Lewis, Charleston, SC (US); Corey Smith, University Heights, OH (US); James Bates, Cleveland, OH (US); Nicole Meyers, Garfield Heights, OH (US); Spencer T. Burton, Cincinnati, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/894,417

(22) Filed: Feb. 12, 2018

(65) Prior Publication Data
US 2018/0164240 A1  Jun. 14, 2018

Related U.S. Application Data

(63) Continuation-in-part of application No. PCT/US2016/053786, filed on Sep. 26, 2016.
(Continued)

(51) Int. Cl.
*G01N 33/543* (2006.01)
*G01N 27/22* (2006.01)
(Continued)

(52) U.S. Cl.
CPC .......... *G01N 33/5438* (2013.01); *G01N 1/14* (2013.01); *G01N 27/226* (2013.01);
(Continued)

(58) Field of Classification Search
CPC ........ G01N 33/54393; G01N 33/5438; G01N 27/227; G01N 2333/70
See application file for complete search history.

(56) References Cited

U.S. PATENT DOCUMENTS 6,458,600 B1 * 10/2002 Mirsky ............... B01J 19/0046
204/194
9,029,168 B2    5/2015 Mcalpine et al.
(Continued)

FOREIGN PATENT DOCUMENTS

| CN | 102000658 A | 4/2011 |
| CN | 102914580 A | 2/2013 |
| CN | 104820093 A | 8/2015 |

OTHER PUBLICATIONS

Liu et al., Application of a novel electrosynthesized polydopamine-imprinted film to the capacitive sensing of nicotine, Analytical and Bioanalytical Chemistry, vol. 385, pp. 724-729. (Year: 2006).*
(Continued)

*Primary Examiner* — Melanie Brown
(74) *Attorney, Agent, or Firm* — Tarolli, Sundheim, Covell & Tummino LLP

(57) ABSTRACT

A sensor for the detection of an analyte in a fluid includes an electrode having a detection surface, a polydopamine layer adhered to the electrode detection surface; and optionally a receptor chemically functionalized to the polydopamine of the detection surface of the electrode. The receptor selectively binds to the analyte of interest and the analyte once bound is detectable by measuring the change of capacitance of the electrode.

20 Claims, 21 Drawing Sheets

Related U.S. Application Data

(60) Provisional application No. 62/457,455, filed on Feb. 10, 2017, provisional application No. 62/222,947, filed on Sep. 24, 2015.

(51) Int. Cl.
  *G01N 33/48* (2006.01)
  *G01N 1/14* (2006.01)
  *G01N 1/40* (2006.01)

(52) U.S. Cl.
  CPC .......... *G01N 27/227* (2013.01); *G01N 33/48* (2013.01); *G01N 33/54373* (2013.01); *G01N 33/54393* (2013.01); *G01N 1/405* (2013.01); *G01N 2333/70* (2013.01)

(56) References Cited

U.S. PATENT DOCUMENTS

| | | | |
|---|---|---|---|
| 9,346,913 B2 | 5/2016 | Yan et al. | |
| 2008/0223734 A1* | 9/2008 | Bayachou | G01N 33/0037 205/781 |
| 2008/0262740 A1* | 10/2008 | Potter | C12Q 1/006 702/19 |
| 2009/0032695 A1* | 2/2009 | Kaye | G01N 27/622 250/281 |
| 2011/0287977 A1* | 11/2011 | Cai | G01N 33/54346 506/13 |
| 2012/0092424 A1* | 4/2012 | Fox | B41J 2/14209 347/71 |
| 2013/0304397 A1* | 11/2013 | Erlandsson | G01N 27/22 702/30 |

OTHER PUBLICATIONS

Dreyer et al., Perspectives on poly(dopamine), Chemical Science, vol. 4, pp. 3796-3802. (Year: 2013).*

Lin et al., Poly(dopamine) coated gold nanocluster functionalized electrochemical immunosensor for brominated flame retardants using multienzyme-labeling carbon hollow nanochains as signal amplifiers, 2013, Biosensors and Bioelectronics, vol. 45, pp. 82-88. (Year: 2013).*

International Search Report & Written Opinion for Application No. PCT/US2016/053786.

* cited by examiner

A
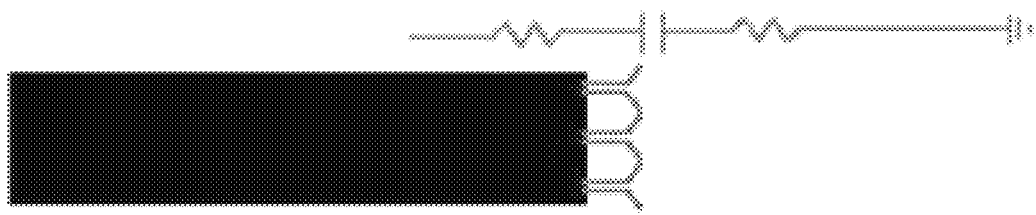
B
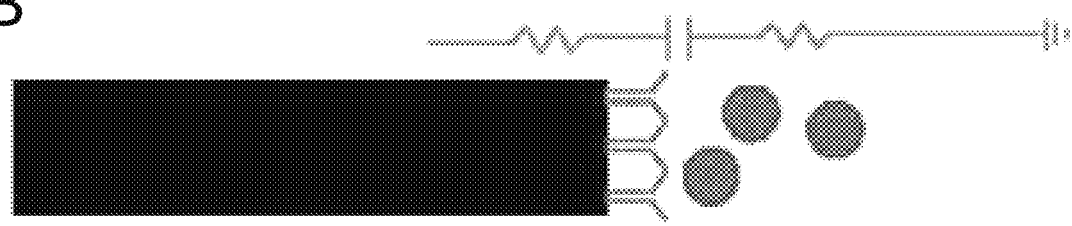
C
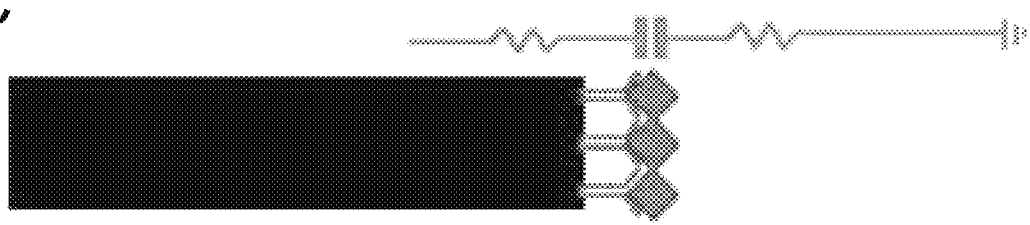
Figs. 7A-C

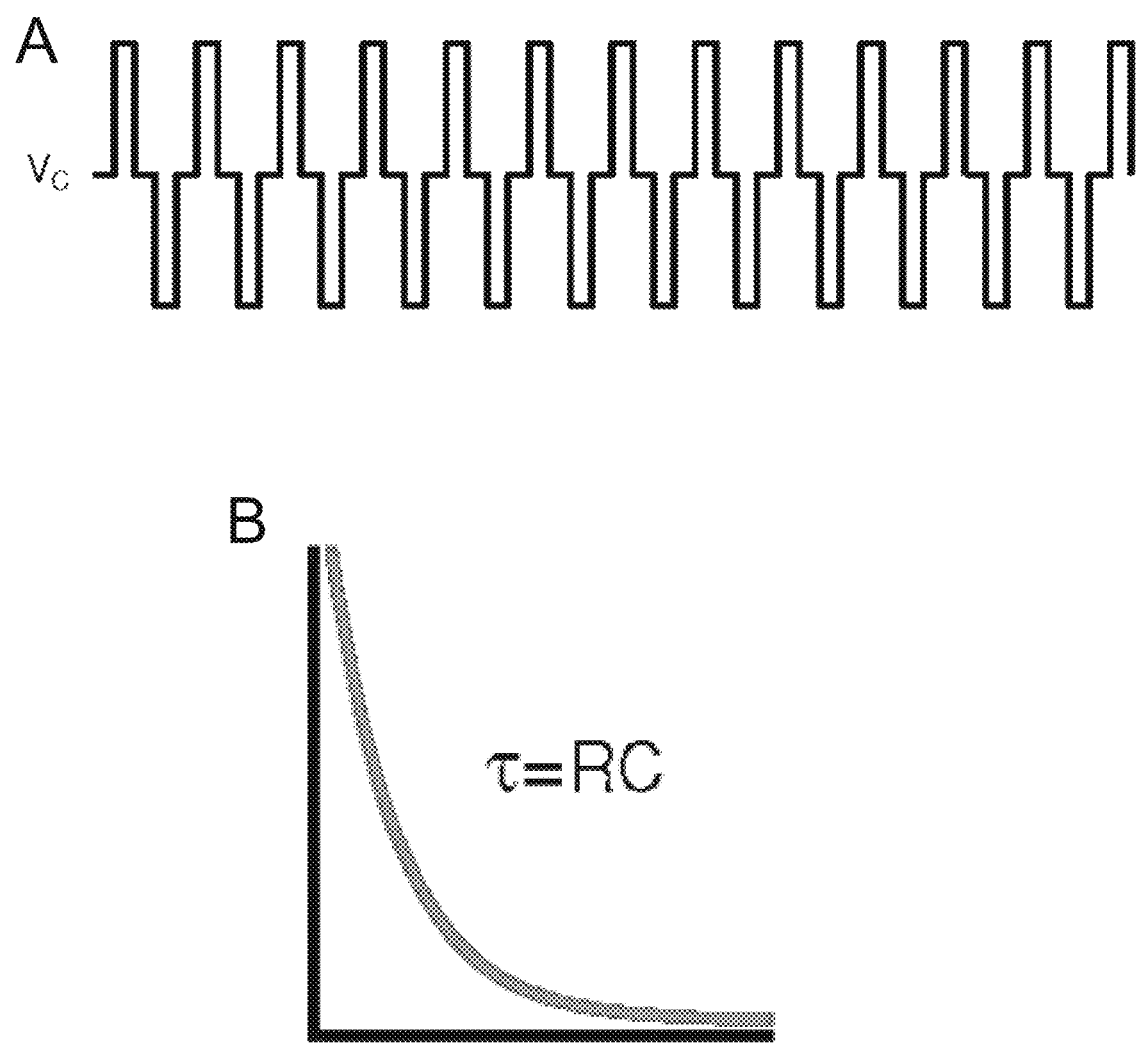
Figs. 8A-B

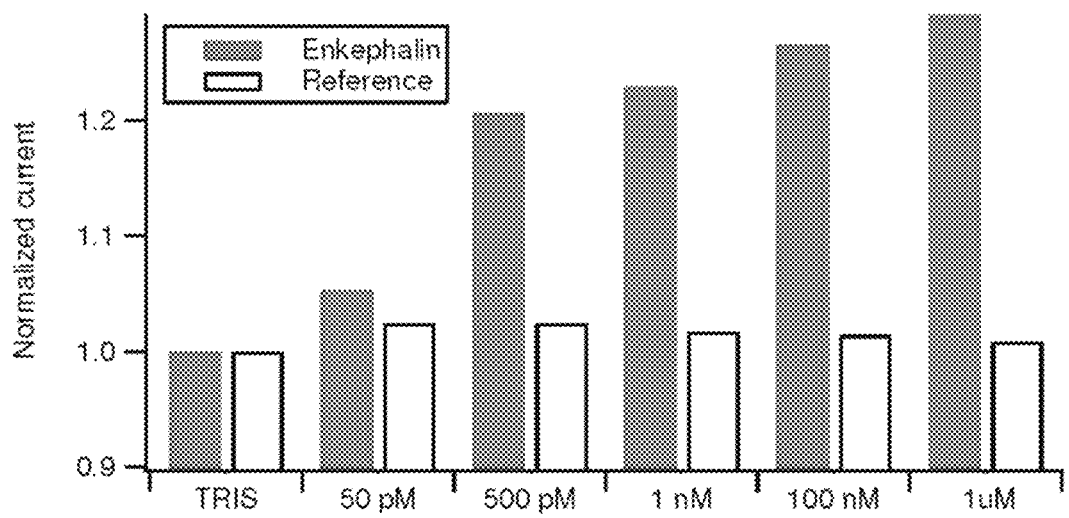
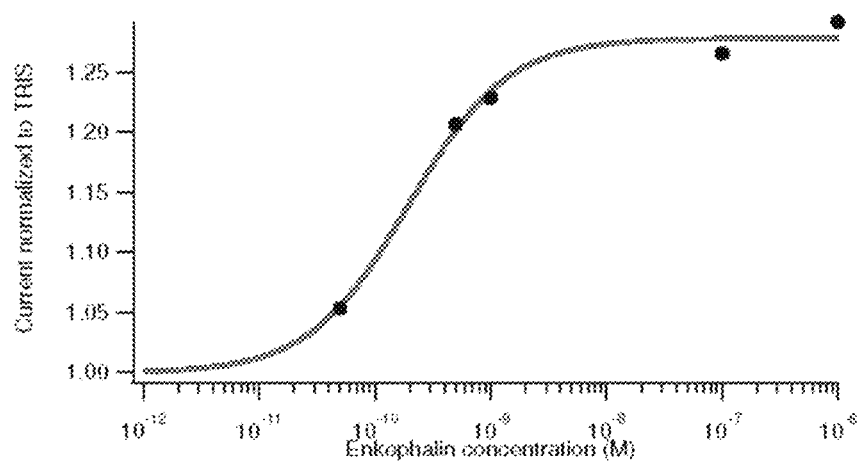
Figs. 10A-B

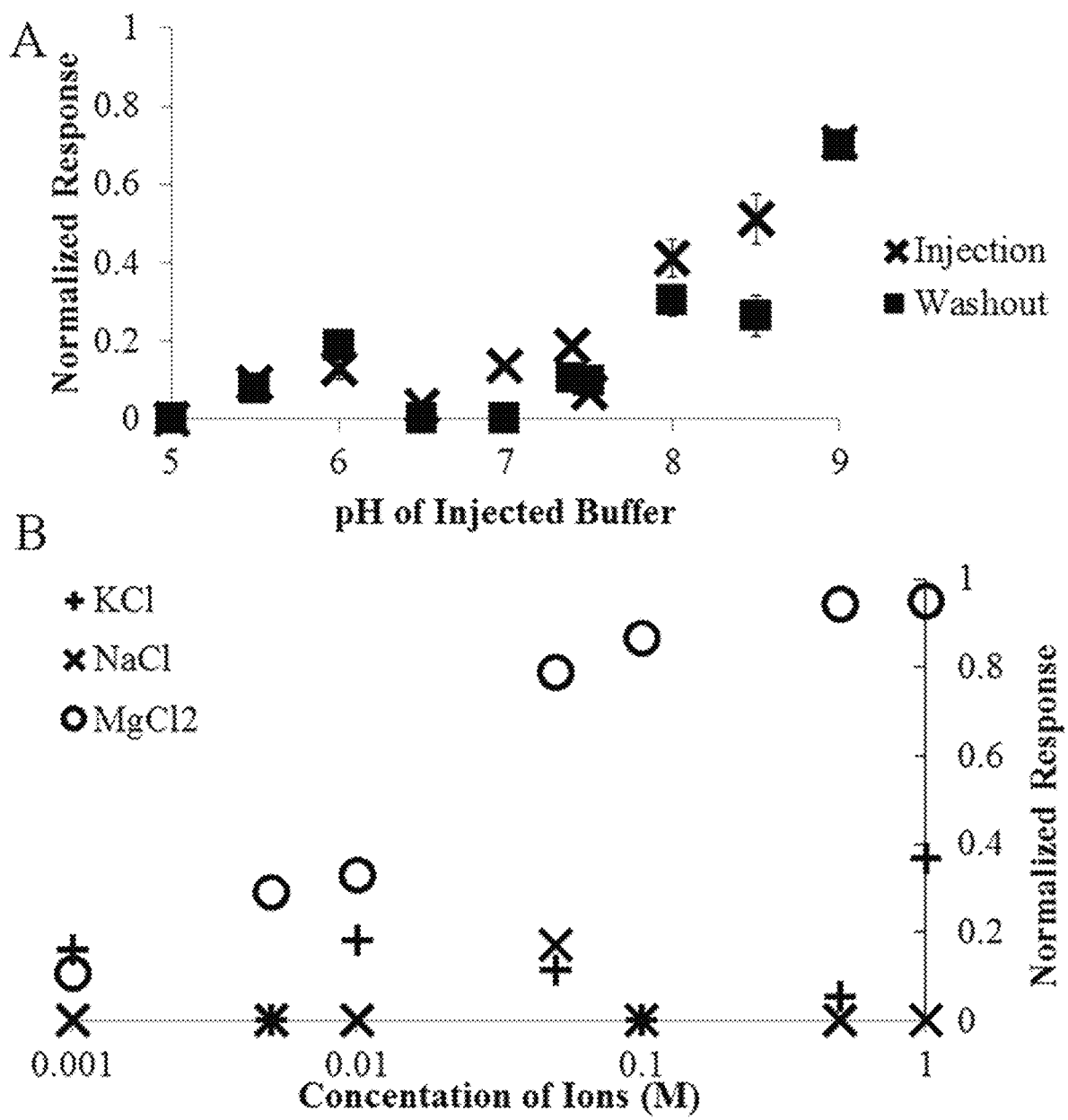
Figs. 21(A-B)

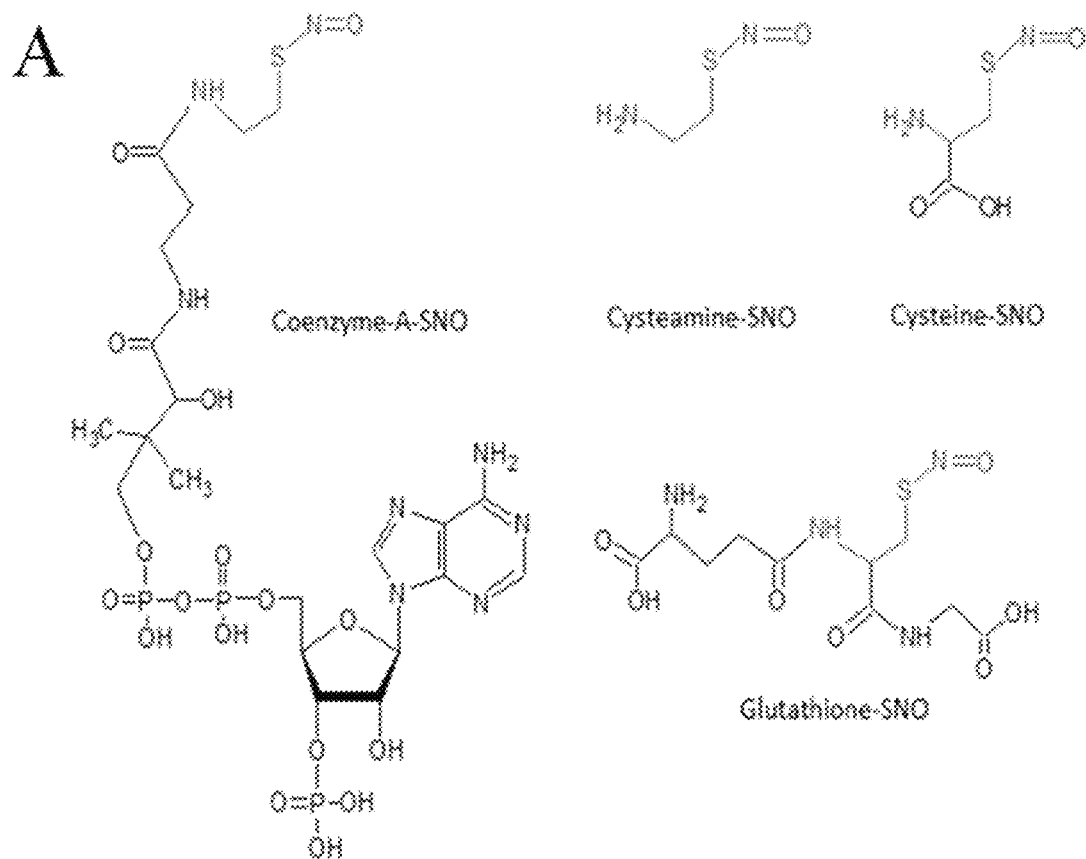
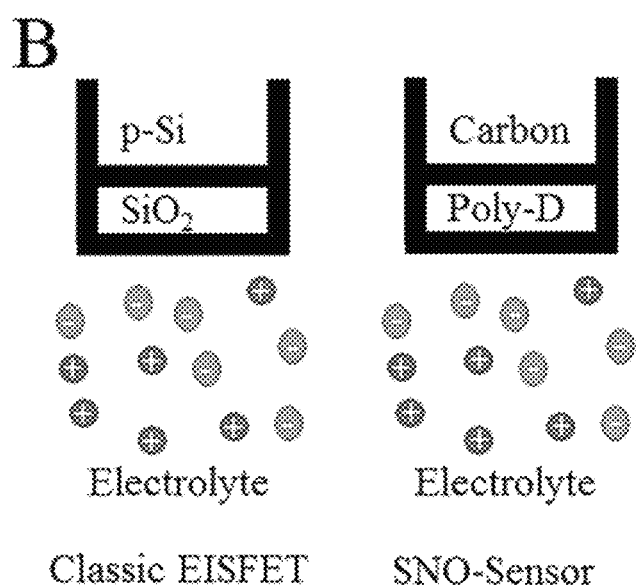
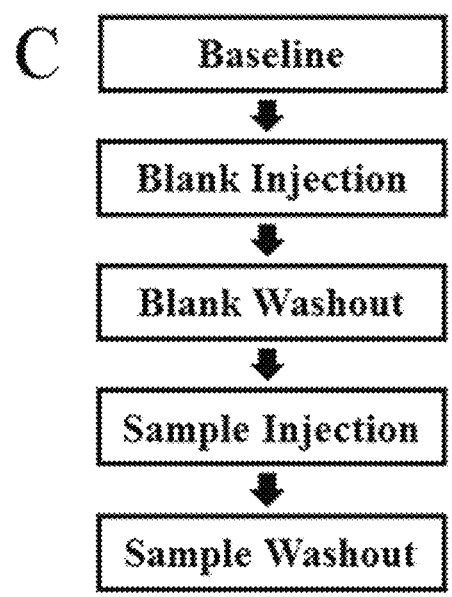
Figs. 22(A-C)

SENSOR FOR DETECTION OF ANALYTES

RELATED APPLICATION

This application is a continuation-in-part of International Patent Application No PCT/US2016/053786 filed Sep. 26, 2016, which claims priority from U.S. Provisional Application No. 62/222,947, filed Sep. 24, 2015; and this application also claims priority from U.S. Provisional Patent Application No. 62/457,455, filed Feb. 10, 2017, the subject matter of which are incorporated herein by reference in their entirety.

GOVERNMENT FUNDING

This invention was made with government support under Grant No. R01-GM102191 awarded by The National Institutes of Health/National Institute of General Medicine Sciences. The United States government has certain rights to the invention.

BACKGROUND

A biosensor can determine the existence or the concentration of a certain analyte in a sample by translating molecular recognition of the analyte ultimately into an electrical signal by means of a translation system. Biosensors can be used for any kind of analyte that can be detected by biological means. Analytes that can be detected and quantified include metabolites, drugs, proteins, antigen-antibody interactions. For example, glucose can be detected in a diabetes patient's blood, life-threatening micro-organisms can be detected in food to enhance food safety, pollutants like CO, herbicides, chemicals and heavy metals can be detected to find and decontaminate polluted areas.

Biosensors can be catalogued in different groups, depending on their biological recognition system and the translation system.

Biological recognition system can include enzymatic sensors (based upon the reaction of a substrate catalysed by an enzyme, immunosensors (based upon the affinity between antibodies (or parts thereof) and antigenic determinants, e.g., ELISA test) and genosensors (based e.g., upon recognition of complementary RNA and/or DNA single strand molecules, and DNA-probes).

Translation systems can include electrochemical biosensors (amperometric, potentiometric, capacitive or impedimetric), optical biosensors (e.g., Surface Plasmon Resonance (SPR), ellipsometric, or fluorescence), gravimetric biosensors (measuring a difference in mass by measuring a change in resonance frequency of a quartz crystal when the analyte binds or adsorbs to the crystals), and calorimetric biosensors (measuring the reaction enthalpy released when the analyte binds to a substrate).

When using recognition biomolecules, such as antibodies, enzymes, oligonucleotides or nucleic acids, these molecules need to be fixed to a carrier surface in order to be able to perform their detection function in a reproducible way. Several possible techniques have been devised to perform the immobilisation.

One technique that is used is immobilisation of the biomolecule between two selectively permeable membranes. Another technique relies on physical adsorption to a fixed carrier surface. A third technique is based upon bifunctional reagents that can couple molecules to each other. Another technique is covalent binding to a substrate.

SUMMARY

Embodiments described herein relate to capacitive or impedimetric sensors or biosensors that are capable of providing analysis of various analytes or biomolecules in a fluidic sample or solution, such as biological or bodily fluids, using chemical or biological recognition elements. The biosensor can produce a signal that is related to the presence or quantity of the analytes being detected in a biological sample, such as a bodily fluid. In some embodiments, the biosensor can be used to detect the presence small molecules, proteins, polypeptides, cytokines, microorganisms, polynucleotides (mRNA, DNA, cDNA, mRNA, etc.) that are present in a biological sample, such as a bodily fluid (e.g., serum, blood, plasma, saliva, urine, mucous, etc). The biosensors can advantageously be used in vivo or ex vivo to provide a cost-effective means for simple point-of-care, real time assessment of analytes in biological samples, such as bodily fluids obtained by non-invasive or minimally invasive means, or for in vivo diagnostic purposes.

In some embodiments, the sensor includes a sensing electrode and a polydopamine semiconductive polymeric layer that is provided on a sensor active region of the electrode. Optionally, a receptor for an analyte or biological molecule of interest, can be functionalized or chemically functionalized to the sensor active region of the electrode using the polydopamine semiconductive polymeric layer. In other embodiments, the polydopamine semiconductive polymeric layer can act as a reactive surface for binding of an analyte.

During operation, the biosensor can be placed in a fluid, such as a bodily fluid, that includes an analyte or biomolecule of interest. An altered dielectric at the electrode's surface active region caused by binding or complexing of the analyte or biomolecule in the fluid with the receptor and/or polydopamine semiconductive polymeric layer can be used to detect the presence of the analyte or biomolecule. Binding of the analyte or biomolecule to the receptor and/or polydopamine semiconductive polymeric layer can push high dielectric water in the fluid further away from the receptor and/or polydopamine semiconductive polymeric layer on the sensor active region and replace it with the lower dielectric of the analyte or biomolecule, decreasing capacitance. Additionally, analyte or biomolecule binding to the receptor and/or polydopamine semiconductive polymeric layer can change the conformation of the polymeric layer, altering the capacitance further. This change in capacitance can be measured to determine the presence and/or concentration of the analyte or biomolecule in the fluid.

In other embodiments, the sensor can include a reference electrode with a polydopamine coating having a thickness, which turns it into a semiconductor. The sensing and reference electrodes can be charged using a Silver/Silver Chloride pellet when provided in a biological solution of interest. The direct current injection charges the sensing and reference electrode and both electrodes are allowed to discharge with their maximum discharge current when the electrodes are charged with a positive current and with a negative current. The combination of these two discharge currents serves as a signal. The sensing and reference electrode signals are collected and amplified independently of each other and then the difference is taken digitally to determine the presence of nonspecific binding to the electrodes. The asymmetry in discharge from a negative and positive current charge takes advantage of the gating potential of the polydopamine/electrode junction, which the sensors at rest sit close to. The signal is derived from the fact the charge brought by the analyte or biomolecule binding moves the polydopamine/electrode junction closer to its gating potential and hence produces an asymmetric response. This provides a time domain signal, which can be used to determine both the presence of attomolar concentrations of an analyte or biomolecule as well as determine its concentration, by taking advantage of the slow on-rate of the receptor and/or polydopamine to the analyte or biomolecule.

The use of a direct current injection into both a sensing and reference electrode, then employing separate signal amplification provides a novel technique for sensing the analyte or biomolecule. The signal itself comes from a novel mechanism by means of examining the distance from the junction potential by measuring the charge asymmetry upon the sensor discharging after experiencing a positive or a negative current.

BRIEF DESCRIPTION OF THE DRAWINGS

FIGS. 7(A-C) illustrate a schematic representation of the impedimetric antibody-based detection technique.

FIGS. 8(A-B) illustrate plots showing that the capacitance at the electrode-solution interface was sampled by a step depolarization in the electrode-ground circuit (Vc=voltage command).

FIGS. 10(A-B) illustrates a graph and plot showing Increasing concentrations of enkephalin increased the current measured in the enkephalin electrode (grey bars) but not the control GAPDH electrode (white bars).

FIGS. 21(A-B) illustrate plots showing the average normalized response of the sensing electrodes to blank running buffer injections of varying pH (A) or with various concentrations of potassium, sodium, or magnesium (B).

FIGS. 22(A-C) illustrate (A) diagrams of endogenous small molecule SNOs, (B) Schematic of the classic EISFET compared to the polydopamine coated sensor used in SNO detection, and (C) the data collected during a single sensing experiment.

DETAILED DESCRIPTION

Figure 1:
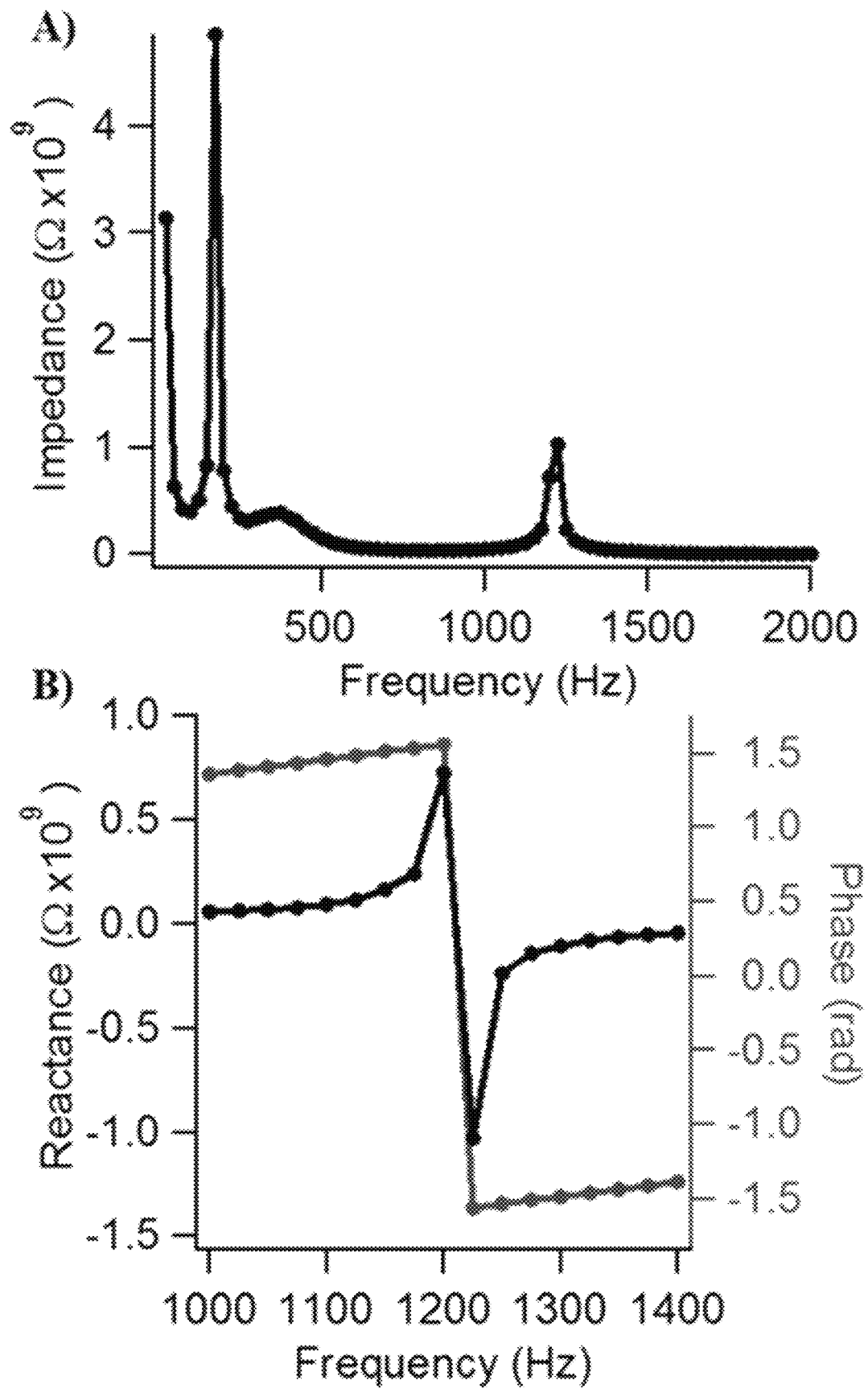
FIGS. 1(A-B) illustrate plots showing naïve carbon fibers display a distinct anti-resonance peak at high frequencies. Frequency response was gathered from 25-2000 Hz at 25 Hz increments and 32 cycles per frequency. (A) Impedance response of the naïve carbon fiber in a TBS solution. (B) The reactance of the impedance peak between 1 and 1.4 kHz and the phase angle at corresponding frequencies.

Unless specifically addressed herein, all terms used have the same meaning as would be understood by those of skilled in the art of the subject matter of the application. The following definitions will provide clarity with respect to the terms used in the specification and claims.

The term "bodily sample" refers to a sample that may be obtained from a subject (e.g., a human) or from components (e.g., tissues) of a subject. The sample may be of any biological tissue or fluid with which biomarkers described herein may be assayed. Frequently, the sample will be a "clinical sample", i.e., a sample derived from a patient. Such samples include, but are not limited to, bodily fluids, e.g., saliva, breath, urine, blood, plasma, or sera; and archival samples with known diagnosis, treatment and/or outcome history.

The term "biological sample" denotes a substance that contains the bio-molecules to be analyzed (for instance, blood plasma, saliva, urine, food, samples, etc., usually after pre-processing). The biological sample can encompass any material derived by processing the bodily sample. Processing of the bodily sample may involve one or more of, filtration, distillation, extraction, concentration, inactivation of interfering components, addition of reagents, and the like.

The terms "control" or "control sample" refer to one or more biological samples isolated from an individual or group of individuals that are normal (i.e., healthy). The term "control", "control value" or "control sample" can also refer to the compilation of data derived from samples of one or more individuals classified as normal.

The term "biological molecules" or "biomolecules" may particularly denote any molecules, which play a significant role in biology or in biological or biochemical procedures, such as DNA, RNA, proteins, enzymes, cells, bacteria, virus, etc.

The term "sensor" may particularly denote any device, which may be used for the detection of the presence/absence or even the concentration of analytes or biomolecules.

The term "biosensor" may particularly denote any device, which may be used for the detection of an analyte comprising biological molecules, such as DNA, RNA, proteins, enzymes, cells bacteria, virus, etc. A biosensor may combine a biological component (for instance capture molecules or receptors or ligand receptors at a sensor active surface capable of detecting molecules) with a physiochemical or physical detector component (for instance a capacitor having a capacitance which is modifiable by a sensor event).

The term "S-nitrosothiols," as used herein, means a group of organic sulfur containing nitrites, alkyl thionitrites, including S-nitroso-N-acetylpenicillamine, S-nitrosoglutathione, S-nitrosocysteine, 5-nitrosoalbumin, nitrosylated proteins, S-nitroso-N-acetyl cysteine, S-nitrosohomocysteine, S-nitros coenzyme A, etc.

The terms "fixation agent or fixing agent," as used herein, means an agent that interacts with free thiols and amines by blocking, binding, fixing or modifying any free thiols or amines in the fluidized biological sample thereby removing the free thiols and aminers or inhibiting same from contributing to the results of the assay.

The terms "fixing," "binding," "blocking," and "modifying," as used herein relative to free thiols and amines, are used interchangeably to mean interacting with the free thiols and amines to inhibit binding of the free thiols or amines to polydopamine.

The term "sensor active region" may particularly denote an exposed region of a sensor which may be brought in interaction with a fluidic sample so that a detection event may occur in the sensor active region. In other words, the sensor active region may be the actual sensitive area of a sensor device, in which area processes take place which form the basis of the sensing.

The term "subject" refers to a human or another mammal, which can be afflicted with a neural injury, such as a traumatic brain injury, but may or may not have such an injury. Typically, the terms "subject" and "patient" are used herein interchangeably in reference to a human individual.

The term "substrate" may denote any suitable material, such as a semiconductor, glass, plastic, etc. According to an exemplary embodiment, the term "substrate" may be used to define or support generally the elements for sensor. Also, the substrate may be any other base on which a electrode is formed or provided within.

The term "fluidic sample" may particularly denote any subset of the phases of matter. Such fluids may include liquids, gases, plasma and, to some extent, solids, as well as mixtures thereof. Examples for fluidic samples are DNA-containing fluids, blood, interstitial fluid in subcutaneous tissue, muscle or brain tissue, urine or other body fluids. For instance, the fluidic sample may be a biological substance. Such a substance may comprise proteins, polypeptides, nucleic acids, DNA strands, etc.

The term "receptor" or "ligand receptor" may particularly denote a molecule that can capture specific target biomolecule or analyte.

Embodiments described herein relate to capacitive or impedimetric sensors or biosensors that are capable of providing analysis of various analytes or biomolecules in a fluidic sample or solution, such as biological or bodily fluids, using chemical or biological recognition elements. The biosensor can produce a signal that is related to the presence or quantity of the analytes being detected in a biological sample, such as a bodily fluid. In some embodiments, the biosensor can be used to detect the presence small molecules, proteins, polypeptides, cytokines, microorganisms, polynucleotides (mRNA, DNA, cDNA, mRNA, etc.) that are present in a biological sample, such as a bodily fluid (e.g., serum, blood, plasma, saliva, urine, mucous, etc). The biosensors can advantageously be used in vivo or ex vivo to provide a cost-effective means for simple point-of-care, real time assessment of analytes in biological samples, such as bodily fluids obtained by non-invasive or minimally invasive means, or for in vivo diagnostic purposes.

In some embodiments, the sensor includes a sensing electrode and a polydopamine semiconductive polymeric layer that is provided on a sensor active region of the electrode. Optionally, a receptor for an analyte or biological molecule of interest, can be functionalized or chemically functionalized to the sensor active region of the electrode using the polydopamine semiconductive polymeric layer. In other embodiments, the polydopamine semiconductive polymeric layer can act as a reactive surface for binding of an analyte.

The term "functionalized" or "chemically functionalized," as used herein, means addition of functional groups onto the surface of a material by chemical reaction(s). As will be readily appreciated by a person skilled in the art, functionalization can be employed for surface modification of materials in order to achieve desired surface properties, such as biocompatibility, wettability, and so on. Similarly, the term "biofunctionalization," "biofunctionalized," or the like, as used herein, means modification of the surface of a material so that it has desired biological function, which will be readily appreciated by a person of skill in the related art, such as bioengineering.

During operation, the bio sensor can be placed in a fluid, such as a bodily fluid, that includes an analyte or biomolecule of interest. An altered dielectric at the electrode's surface active region caused by binding or complexing of the analyte or biomolecule in the fluid with the receptor and/or polydopamine semiconductive polymeric layer can be used to detect the presence of the analyte or biomolecule. Binding of the analyte or biomolecule to the receptor and/or polydopamine semiconductive polymeric layer can push high dielectric water in the fluid further away from the receptor and/or polydopamine semiconductive polymeric layer on the sensor active region and replace it with the lower dielectric of the analyte or biomolecule, decreasing capacitance. Additionally, analyte or biomolecule binding to the receptor and/or polydopamine semiconductive polymeric layer can change the conformation of the polymeric layer, altering the capacitance further. This change in capacitance can be measured to determine the presence and/or concentration of the analyte or biomolecule in the fluid.

As the size of the electrode decreases, capacitances of the electrode decrease accordingly, including a change in capacitance at the surface active region of the electrode upon ligand biding. This creates a lower limit on electrode size possible that still provides adequate signal to noise fidelity. In order to overcome this limitation, the polydopamine semiconductive polymeric layer can be used to chemically functionalize the ligand receptor to the surface active region of the electrode or as the reactive surface for binding of the analyte. This can provide a capacitive sensor with field effect contributions, a hybrid between a purely capacitive and field-effect sensor. What signal is lost in detection surface area can be gained in field-effect.

Advantageously, polydopamine or dopamine films have been shown to form electronic-ionic hybrid conductors, similar to p-type semiconductors. Dopamine contains a catechol and an amine group. In a basic environment it will form a polymer that is adherent to most surfaces. The catechol group of polydopamine can be reactive towards thiol, amino, and imidazole groups under a basic environment. This makes polydopamine an ideal immobilization polymer to bind S-nitrosothiols as well as a wide range of ligand receptors to the electrode surface as any protein in solution will bind with the polydopamine layer.

Coating a sensor active region of the electrode with a polydopamine layer can make a capacitive sensor with a semiconductor-like region that can bind S-nitrosothiols in a sample and that can be easily functionalized with a large variety of ligand receptors.

In some embodiments, the electrode can be functionalized with a ligand receptor, such as an antibody (e.g., pituitary adenylate cyclase activating protein (PACAP) IgG antibody) to sense a ligand (e.g., PACAP ligand) in solution. Upon ligand binding, resulting changes in capacitance of the electrode can be detected using, for example, a variance analysis method that adopts a software lock-in approach. This approach provides a simple and sensitive method for detection of the analyte or biomolecule in solution. The sensitivity of the sensor can be dependent on the binding receptor, in this instance an IgG antibody, and provide adequate signal when presented with ligand in the nanomolar range.

In some embodiments, the electrode can have a surface active region that is defined by an insulator or dielectric that covers at least a portion of the electrode. The surface active region can have an area comparable to that of the cross-section of a carbon microfiber. Small physical dimensions may be advantageous to achieving nanomolar-molecule resolution. The smaller the electrode size, the higher the relative capacitance change as a result of a molecule capture.

The footprint area of a captured ligand on the electrode area may determine the corresponding capacitance change. All electrode area that is not covered by the ligand receptor may in fact act as a parasitic capacitance in parallel to the capacitance change due to the single-molecule capture. That is why the electrode area should be as small as possible. A specifically appropriate electrode is as small as a molecule, provided the electrode pitch is small enough to ensure a reasonable surface coverage. The detectability of single molecules is a matter of achieving high-enough signal-to-noise ratio.

In some embodiments, the electrode may be a micron or sub-micron electrode. In other words, the electrode may have linear dimensions in the order of magnitude of several micrometers or less. Particularly, the electrode can be a microelectrode and, particularly, can have dimensions in a range of essentially one micrometer to ten micrometers.

The electrode may comprise an electrically conductive material, for instance, a material selected from the group consisting of gold, silver, platinum, palladium, carbon, indium tin oxide, alloys thereof, and composites thereof. In some embodiments, the electrode can include, carbon based materials, such as carbon fibers having micron dimensions.

In some embodiments, the electrode can be provided or formed on a substrate formed of electrically non-conductive material, such as glass, silica, alumina, ceramic based materials or a electrically non-conductive polymer, or a semiconductive substrate, such as silicon. The electrode can be made using a thin film, thick film, and/or ink-jet printing technique, especially for the deposition of multiple electrodes on a substrate. The thin film process can include physical or chemical vapor deposition.

In other embodiments, the electrode can be formed from a carbon fiber with a cross-sectional diameter on a micron scale, e.g., about 5 µm to about 10 µm. The carbon fiber can be encapsulated or ensheathed with an insulator so that the tip of fiber is exposed. The fiber tip can form a surface active region of carbon fiber electrode.

Exposed regions that define surface active regions of the electrode can be coated with a microlayer or nanolayer of polydopamine by immersing the exposed surface of the electrode in a solution in which dopamine or a derivative thereof is dissolved. In some embodiments, the solution containing dopamine or the derivative thereof dissolved therein may have a pH of about 7 to about 10. When the pH of the solution is within the range described above, the dopamine or the derivative thereof may be self-polymerized.

Specifically, dopamine can be used in a state of being dissolved in a distilled water-based buffer solution (e.g., 10 mM Tris buffer solution, pH 8.5), which is inexpensive and environmentally friendly, instead of commonly used organic solvents, which are expensive and environmentally harmful. Dopamine is used in this state because the solution with dopamine dissolved therein needs to be maintained in a weak base state (e.g., pH 8.5) to form a layer coated with polydopamine through self-polymerization of dopamine.

In other embodiments, polydopamine can be provided on a surface active region of the electrode using an electrochemical method. As described in Example 1, the electrochemical method was used to deposit polydopamine on an uninsulated tip of a 5 µm carbon fiber electrode. Briefly, the surface active region of the electrode can be placed in a phosphate buffered dopamine solution. A sawtooth voltage waveform (e.g., between 650 mV and −600 mV at 20 mV/sec) can then be applied to the electrode. The evoked current response is proportional to the amount of polydopamine deposited on the electrode. Polydopamine deposition can be calculated after every voltage cycle as the cumulative charge and current response. The deposition can be stopped when current response is about 80% of maximum current response, i.e., prior to deposition of polydopamine on the electrode.

Polydopamine formed by the self-polymerization of dopamine may form a polydopamine layer on the surface active region of the electrode. The polydopamine layer may completely cover the surface active region of the electrode. In some cases, the polydopamine layer may partially cover the surface active region of the electrode. The polydopamine layer may have a thickness of 0.01 µm to 5 µm.

In some embodiments, the ligand receptor, which can be functionalized or chemically functionalized to the electrode using polydopamine, can be any molecule that binds selectively to an analyte of interest. A ligand receptor that binds selectively to an analyte is a molecule that binds preferentially to that analyte (i.e., its binding affinity for that analyte is greater than its binding affinity for any other analyte). Its binding affinity for the analyte of interest may be 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 100-fold or more than its binding affinity for any other analyte. In addition to its relative binding affinity, the receptor may also have an absolute binding affinity that is sufficiently high to efficiently bind the analyte of interest (i.e., it must have a sufficient sensitivity). Receptors having binding affinities in the picomolar to micromolar range are suitable. Such interaction can be reversible.

The ligand receptor may be of any nature (e.g., chemical, nucleic acid, peptide, polypeptide, lipid, combinations thereof and the like). The analyte too may be of any nature provided there exists a receptor that binds to it selectively and in some instances specifically. In some embodiments, the analyte can be a charged species or molecule.

It will be appreciated, the flexibility of the chemical functionalization using polydopamine makes the sensor useful for attaching essentially any ligand receptor or ligand having an affinity for analytes. Examples of analytes for which receptors or ligands having affinity therefor may be attached to the working electrode include, but are not limited to DNA, oligonucleotides, proteins, biotin, and streptavidin. The receptors for these analytes chemically functionalized to the electrode using polydopamine can include ligands, such as aptamers, oligomers, polymers, catalysts, cells, bacteria, viruses, enzymes, proteins, heptans, saccharides, lipids, glycogens, enzyme inhibitors, enzyme substrates, neurotransmitters, hormones, antigens, antibodies, DNA, and/or RNA. Proteins, including antibodies, generally have several primary amines in the side chain of lysine (K) residues and the N-terminus of each polypeptide can be available for linking to the catechol groups of the polydopamine. Chemical functionalization using polydopamine also enables the bioconjugation of DNA aptamers having an amino group. These aptamers could potentially bind small molecules and proteins.

In some embodiments, the receptor can be an antibody specific for an analyte of interest. Suitable antibodies for use in the sensors and methods described herein include monoclonal and polyclonal antibodies, immunologically active fragments (e.g., Fab or (Fab)2 fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czernik et al., NeuroNeuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the methods described herein can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof is bound. The bound antibodies can then be eluted from the column using a buffer with a high salt concentration.

Instead of being prepared, antibodies to be used in the methods described herein may be obtained from scientific or commercial sources.

It will be appreciated that the receptors are not limited to antibodies or antigen binding fragments and that other receptors to other biomarkers associated with other diseases, disorders, conditions, or pathologies which can be detectable in a bodily sample can also be functionalized or chemically functionalized to the electrode.

In other embodiments, the polydopamine can itself act as a receptor for an analyte of interest. In this embodiment, the specific interaction between polydopamine and S-nitrosothiols allows the polydopamine itself to act as a robust histochemical sensor for nitrosothiols, sidestepping the problem of producing reliable antibodies against SNOs, which is required for functionalizing FET capacitive sensors.

In some embodiments, the electrode can be attached to a detection means, such as an external circuit, for detecting a change in an impedance/capacitance of electrode caused by binding of an analyte of interest to the receptor. For convenient attachment, the electrode can be electrically connected to conducting pads formed by methods, such as evaporation, soldering, chemical vaporization and the like.

A voltage can be applied to the electrodes at a specific frequency and the presence of the target analytes of interest can be sensed by monitoring the capacitance of the electrodes using, for example, variance analysis methods. Upon ligand or analyte binding to the polydopamine layer or receptors, resulting changes in the equivalent circuit are detected using a variance analysis methods adopted from a software lock-in approach. Sensitivities are dependent on the binding receptor and can provide adequate signal when presented with ligand in the attomolar or nanomolar range.

The sensor may be adapted as a biosensor, particular as a single molecule biosensor, which is able to detect even the presence of attomolar or nanomolar concentrations of select molecules in a biological sample, such as biological fluid. In some embodiments, the biosensor can be used in vivo to detect the presence of a biomolecule or analyte in a subject. In other embodiments, the biosensor can be used ex vivo to detect a biological molecule of a biological sample obtained form a subject.

Figure 6:
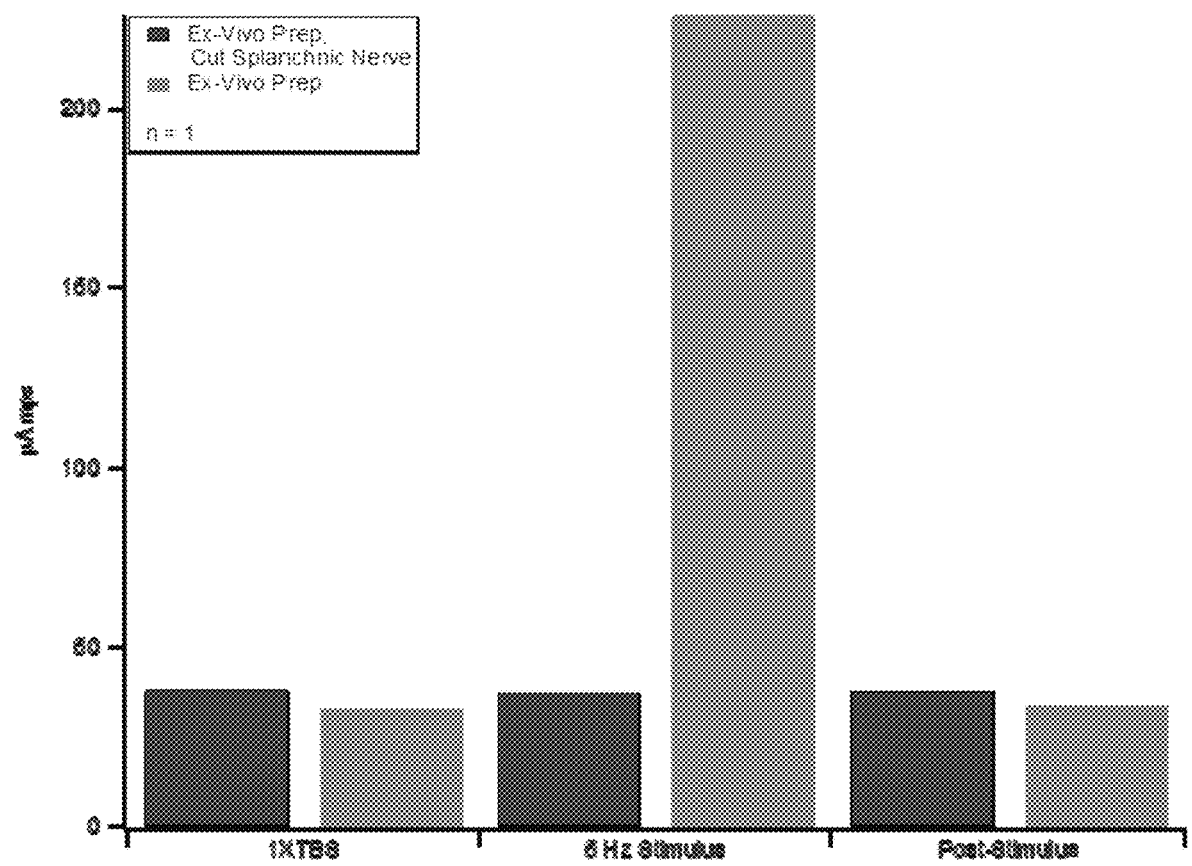
FIG. 6 illustrates a graph showing the measurement of the release of Enkephalin in response to nerve stimulation with a 200 μAmp step function at 5 Hz using a sensor in accordance with an embodiment described herein.

By way of example, FIG. 6 shows the results of an ex vivo experiment measuring the release of Enkephalin in response to nerve stimulation with a 200 µAmp step function at 5 Hz using a sensor in accordance with an embodiment described herein. In this Example, rat kidneys, a portion of the spine, splanchnic nerve, ribs, and the adrenal gland are removed from the rat and placed in Tris-buffered saline. The adrenal glands are cut to expose the adrenal medulla to the bath. A sensor is positioned close to this cut to measure any release that may be evoked when the splanchnic nerve is stimulated with a 200 µAmp step function at 5 Hz.

Advantageously, the analyte or ligand captured by the receptor can be repelled by increasing the frequency and potential of electrode to allow the electrode to be effectively tuned or to be reused for subsequent applications. As frequency increases and as potential increases across the electrode, a dielectric force repelling the analyte or ligand is increased. This is due to the high dielectric constant of water (80 vs. 2-3 for peptides). Water is more attracted and displaces the analyte or ligand. Altering the sinusoidal potential alters the force opposing the natural diffusion of these analyte or ligand in solution. At high potentials or frequencies, the effective concentration of any analyte or ligand near the electrode would be zero. By altering the potential, the concentration of the analyte or ligand near the electrode can be altered and the electrode can be effectively tuned to a concentration range of choosing.

In some embodiments, a plurality of electrodes or capacitive biosensors can be provided on a surface of a substrate to provide a biosensor array. The capacitive biosensor array can be configured to detect analyte concentration changes in a host of chemical and/or biological processes (chemical reactions, cell cultures, neural activity, nucleic acid sequencing processes, etc.) occurring in proximity to the array. The capacitive biosensor array includes a plurality biosensors arranged in a plurality of rows and a plurality of columns. Each biosensor comprises at least one electrode configured to provide at least one output signal representing the presence and/or concentration of an analyte proximate to a surface of the array. For each column of the plurality of columns or for each row of the plurality of rows, the array further comprises column or row circuitry configured to provide source voltage to respective electrodes in the column or row. Each electrode in the row or column can potentially detect a different analyte.

In other embodiments, the capacitive biosensor can include more than one sensing electrode for the detection of the analyte of interest. Single electrode sensors can be prone to both false positives and false negatives due to minor fluctuations in the local charge environment around the sensing electrode's tip. These problems can be minimized by having more than one sensing electrode (e.g., three separate sensing electrodes) which all sense the same environment independently of each other. This, when combined with a continuous sampling method, allows the sensor to take a consensus of the multiple electrodes (e.g., three electrodes) and compare any signal they may produce to the time when a sample is tested. The combination of the continuous sampling and the multiple electrode setup facilitates the elimination of false readings due to over sensitivity of an individual sensing electrode.

In other embodiments, the sensor can also include at least one reference electrode with a polydopamine coating having a thickness, which turns it into a semiconductor. The sensing and reference electrodes can be charged using a Silver/Silver Chloride pellet when provided in a biological solution of interest. The direct current injection charges the sensing and reference electrode and both electrodes are allowed to discharge with their maximum discharge current when the electrodes are charged with a positive current and with a negative current. The combination of these two discharge currents serves as the signal. The sensing and reference electrode signals can be collected and amplified independently of each other and then the difference can be taken digitally to determine the presence of nonspecific binding to the electrodes. The asymmetry in discharge from a negative and positive current charge takes advantage of the gating potential of the polydopamine/electrode junction, which the sensors at rest sit close to. The signal is derived from the fact the charge brought by the analyte binding moves the polydopamine/electrode junction closer to its gating potential and hence produces an asymmetric response. This provides a time domain signal, which can be used to determine both the presence of attomolar concentrations of an analyte as well as determine its concentration, by taking advantage of the slow on-rate of the ligand receptor to the analyte.

The use of a direct current injection into both a sensing and reference electrode, then employing separate signal amplification provides a novel technique for sensing the analyte. The signal itself comes from a novel mechanism by means of examining the distance from the junction potential by measuring the charge asymmetry upon the sensor discharging after experiencing a positive or a negative current.

In some embodiments, a plurality of capacitive biosensors can be provided on a surface of a substrate to provide a biosensor array. The sensor itself relies on the reference electrode which has no ligand receptor attached to it which allows us to determine the signal given by nonspecific binding of analytes or biomolecules in biological fluids. This reference can be used with multiple electrodes at a time. Hence, a sensor, which has any number of sensing electrodes (e.g., three sensing electrodes) and a single reference can be readily designed. This allows us the simultaneous testing of a fluid for several compounds at once. This is done by injecting a single current into a bath and measuring the restoring current produced by amplifiers attached to each electrode. These currents can be recorded and the single reference will be digitally subtracted from each of the signals separately. In this way, almost any number of electrodes can be provided in a single biological sample.

Figure 14:
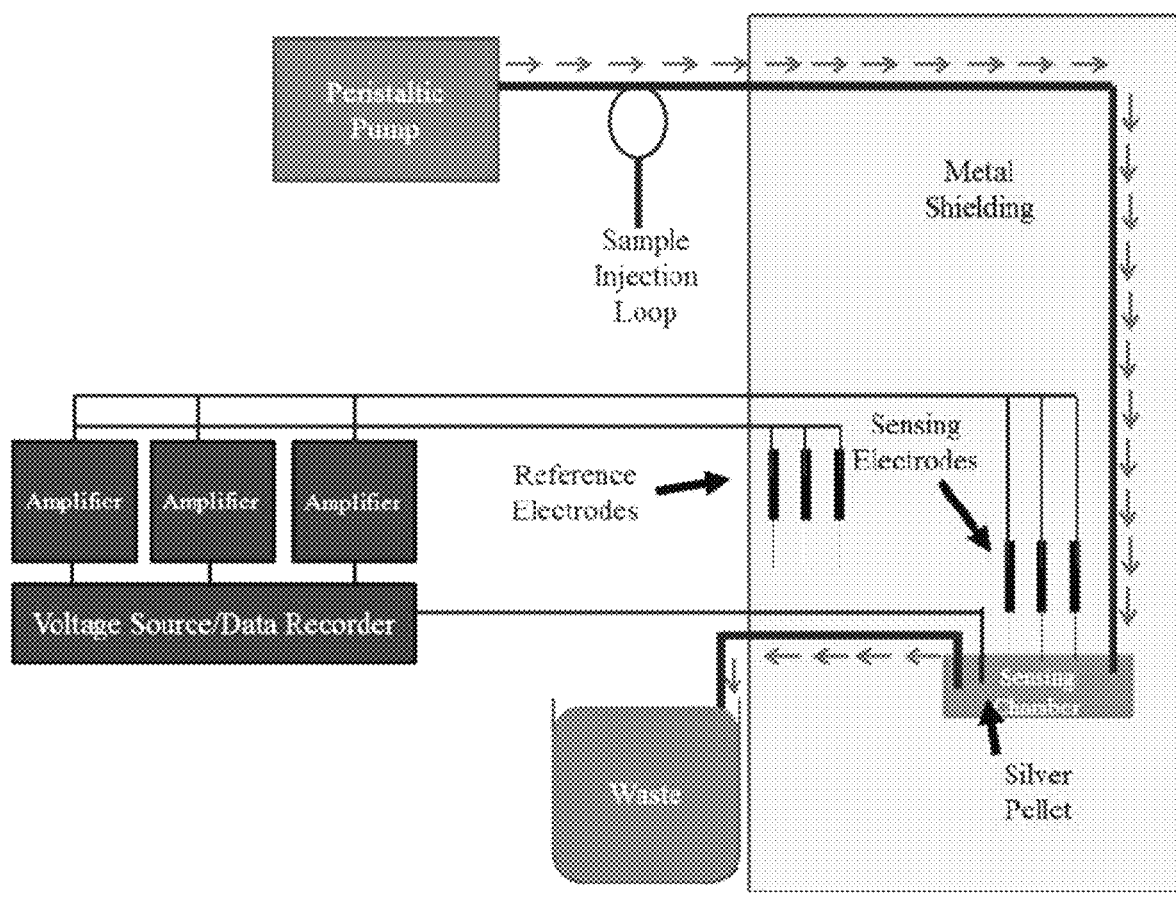
FIG. 14 is a schematic illustration of a capacitive sensor in accordance with an embodiment described herein.

FIG. 14 illustrates a capacitive sensor with a continuous flow set up in accordance with an embodiment of the application that includes a sensing electrode and a polydopamine layer coating a sensing region of the electrode. The capacitive sensor includes a sample injection system, a sensing chamber, and a detection system.

The sample injection system includes a pump that supplies buffer and an injected sample to the sensing chamber, and a sample injection loop for injecting the sample into the system. The pump can include, for example, a peristaltic pump that flows running buffer (e.g., 10 mM Phosphate Buffer, 138 mM NaCl, 2.7 mM KCl, 0.8% Formaldehyde, pH 7.4) continuously into the sensing chamber. This ensures that electrodes in the sensing chamber are constantly washed with fresh buffer and a single sample injection is rapidly washed out.

The sample injection loop is in fluid communication with the pump and comes directly after the pump to allow for the sample to be injected into the loop. The sample itself can first be diluted 1 to 100 into running buffer and then injected onto the sample injection loop. The sample injected into the sample loop can be sent to the sensing chamber.

The sensing chamber is a fluid filled chamber where fluid containing the injected sample constantly flows from the injection system via the pump to a waste system. The sensing chamber can provide a defined volume for sensing the presence and/or quantity of an analyte in the injected sample. The sensing chamber includes sensing electrodes and a voltage source.

A metal shielding surrounds the sensing chamber and shields the sensing electrodes from electrical noise and provides an airtight chamber.

The voltage source can include, for example, a silver-chloride pellet, that either floods the sensing chamber with negatively charged chloride ions or absorbs them. The voltage source need not be limited to a silver-chloride pellet and can include any voltage source that can change the voltage of the fluid inside of the sensing chamber.

The sensing electrodes can include polydopamine tipped carbon fiber electrodes. These sensing electrodes take advantage of the fact that thin layers of polydopamine are semiconductors, which change their capacitance based on the local charge environment. This class of FET sensor is prone to both false positives and false negatives due to minor fluctuations in the local charge environment around the sensing electrode's tip, which can be minimized by having three separate sensing electrodes, which all sense the same environment independently of each other. This, when combined with the continuous sampling method, allows consensus of the three electrodes and compares any signal they may produce to the time when the sample was injected into the sensing chamber. The combination of the continuous sampling and three electrode setup eliminates false readings due to over sensitivity of an individual sensing electrode.

Three reference electrodes can be connected to amplifiers of detection system. These electrodes can be outside of the sensing chamber to pick up ambient electrical noise, which can then be subtracted out by differential amplification in the amplifiers of the detection system. This is used to subtract out electrical noise, which can be inherent in the system and can come from salt antennas, which are formed by the fluid flow from the pump and to the waste.

In some embodiments, the voltage source can act as a current recorder. This machine sends electrical charges to the silver pellet and reads in the amplified current responses from the three sensing electrodes.

The detection system can include three separate differential amplifier that accept electrical signals from a single sensing and reference electrode each and amplify the difference in current inputs between these electrodes. The resulting amplified current is then fed back into the voltage source and recorded digitally.

During operation, the capacitive sensor can detect S-nitrosothiols levels in a sample, such a bodily sample. By way of example, a base starting concentration of S-nitrosothiols in an original stock solution was provided and then serially diluted until the assumed concentration was 0.1 attomolar (the limit of detection of the sensor). A null hypothesis of the assumed starting concentration was tested by running samples at 0.1 aM, 1 aM, 10 aM, 100 aM, 1 fM, and so on and watching for when the sensor returns a positive signal. The limit of detection of the sensor is reliably 0.1 aM for S-nitroso-glutathione and 1 aM for S-nitroso-cysteine. This is due to the presence of a primary amine next to the S-nitroso group in Cysteine which is absent in Glutathione. Furthermore, the presence of this primary amine changes the way that the sensor responds to the presence of a chemical and allows one to distinguish between primary amine S-nitroso-thiols (SNO-Cysteine, SNO-Cysteamine, SNO-Cysteinylglycine, and SNO-Homocysteine) and secondary amine S-nitroso-thiols (SNO-Glutathione, SNO-Coenzyme A, and SNO-proteins). When these two populations are mixed, the stronger secondary amine signal dominates and masks the weaker primary amine signal.

Figure 15:
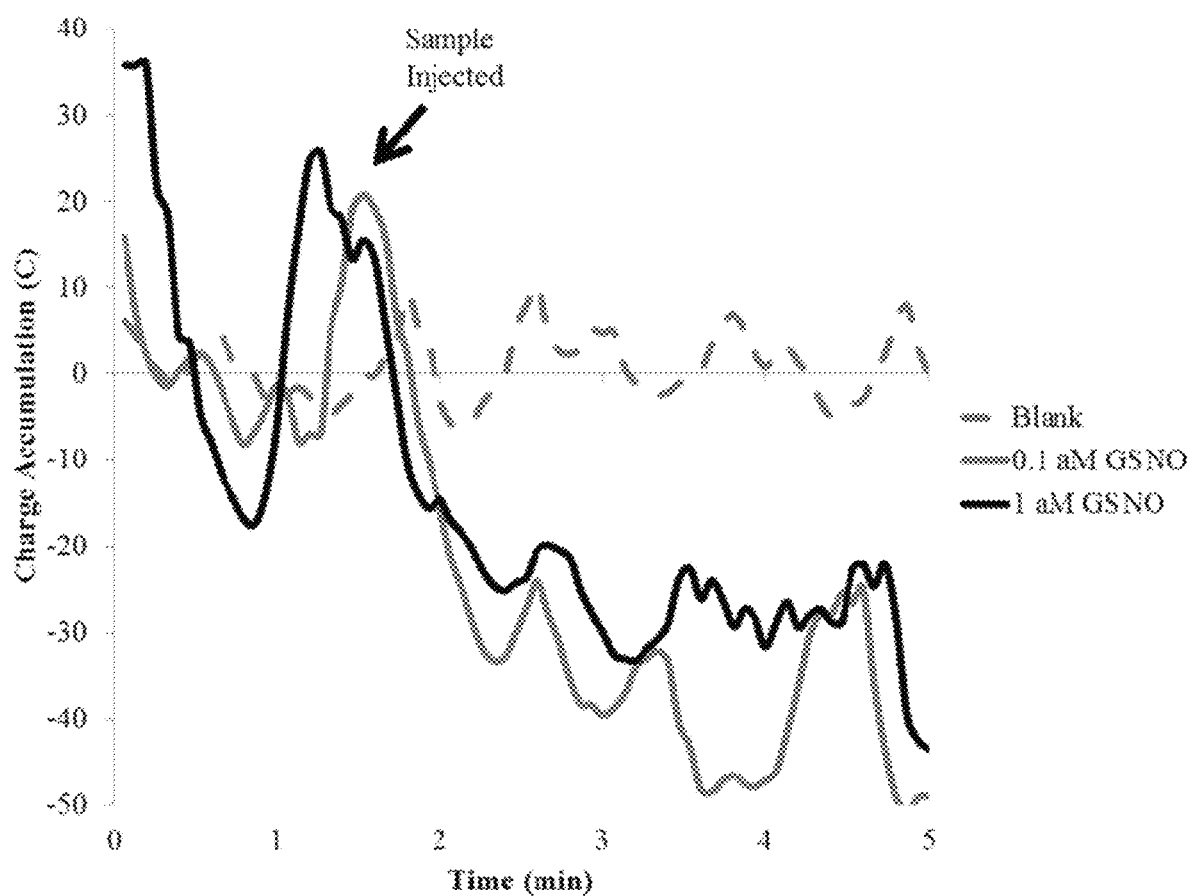
FIG. 15 illustrates a plot of the capacitive sensor response of FIG. 14 to injection of stock nitrosothiol.
Figure 16:
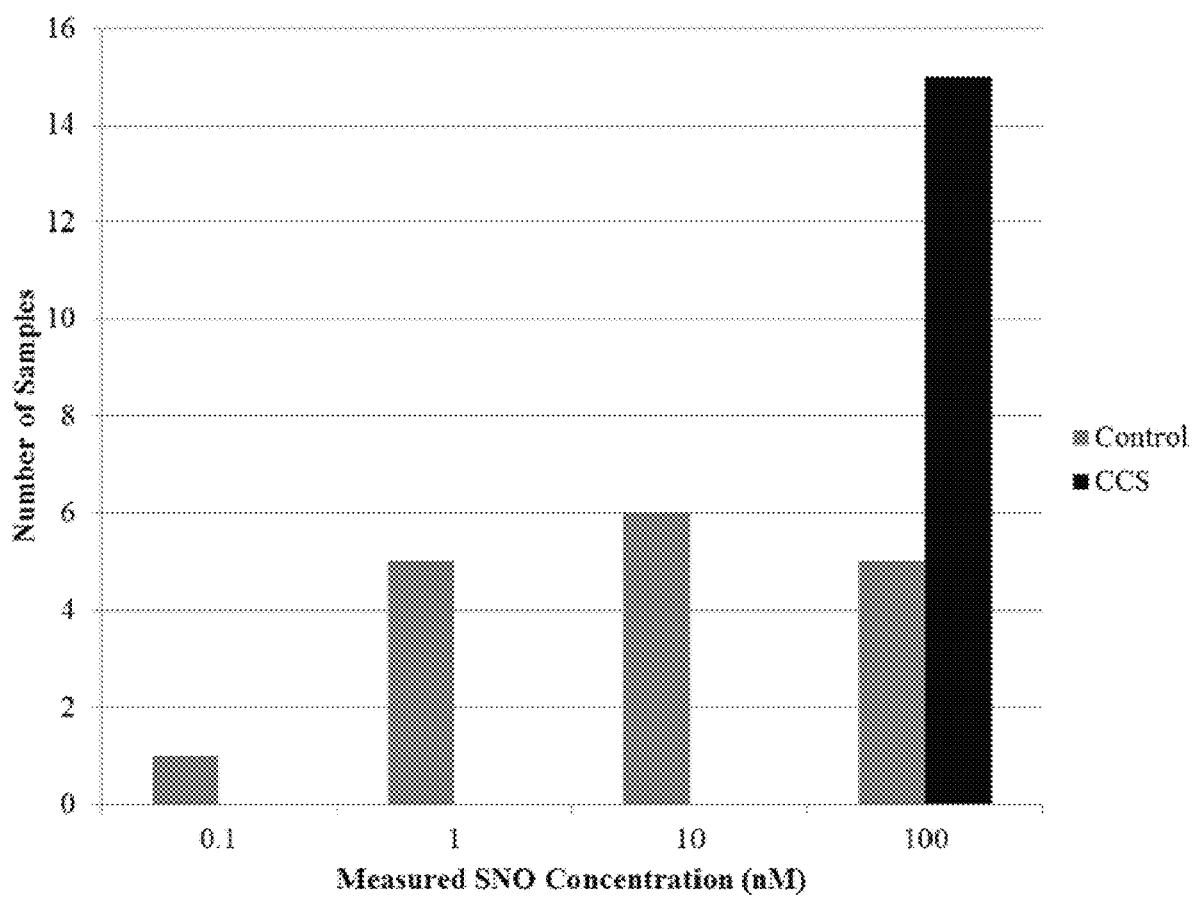
FIG. 16 illustrates a graph of sensor results for cell lysate from airway epithelial cells which were either treated normally or treated with cyclic compressive stress before they were lysed, spun through a 10 kDa filter, diluted into running buffer and injected into the sensing chamber of the capacitive sensor of FIG. 14.

Experiments were done by taking a biological sample and spinning it through a 10 kDa filter to remove all large proteins. The sample was diluted into running buffer and then allowed to sit in the sample injection loop for 5 minutes before sending the sample into the sensing chamber. The capacitive response of the sensing electrodes was then measured and sample, which show a significant change in the total charge accumulation after a single voltage step were considered to be positive signal. FIG. 15 shows a standard plot of total charge accumulation over time starting 2 minutes prior to the sample being sent into the sensing chamber, sensor is insensitive to the concentration of GSNO in solution, returning either a positive or a negative signal. However, since the threshold for detection is reliably 0.1 aM GSNO, a null hypothesis can be formulated about the initial concentration of biological samples. FIG. 16 shows the results for cell lysates of lung epithelial cells that were either allowed to sit normally on their filter or were exposed to cyclic compressive stress to simulate exercise.

Other embodiments described herein relate to a method for screening a biological sample for S-nitrosothiols using the capacitive sensor, described herein, which includes a polydopamine semiconductive polymeric layer that acts a reactive surface for binding of the S-nitrosothiols. In the method, a biological sample is contacted with a fixation agent that binds to or blocks free thiols, primary amines, and secondary amines without binding to or interacting with S—NO bonds in S-nitrosothiols. Blocking free thiols, primary amines, and secondary amines blocks covalent binding of these compounds to catecholamine ring in polydopamine and prevents interactions of the polydopamine surface with these compounds. This means that if a biological sample is treated with the fixation agent, the polydopamine surface will not sense free thiols or amines, and will specifically sense nitrosylated thiols.

Generally, any fixation agent may be used that interacts with or binds free thiols and amines but does not interact with nitrosothiols. The fixation agent can include, for example, paraformaldehyde, formaldehyde, maleimide, diamide, n-ethymaleimide, iodoacetate, iodoacetamide (disulphide thiols), 5',5'-dithio-bis-3-nitrobenzoate (DTNB), 4-(N—(S-glutathionylacetyl)amino)-phenylarsenoxide (GSAO), methyl methanethiolsulphonate (MMTS), 4,4'dithiodipyridine, monoisoamyl 2,3-dimercaptosuccinic acid (MiADMSA), meso-2,3-dimercaptosuccinic acid (DMSA), tris-(2-carboxyethyl)phosphine (TCEP), tris-(2-cyanoethyl) phosphine, dansyl aziridine, acrylodan, 2-aminoethyl-2'-aminoethane thiosulfonate. More preferably, the fixation agent is paraformaldehyde or formaldehyde.

The fixation agent can be added directly to the biological sample or in the alternative the fixation agent can be covalently or non-covalently immobilized on a solid support of a column and the fluidized sample is passed through the column. The term "solid support" may be a purification column, a discontinuous phase of discrete particles, a membrane or filter. Examples of materials for forming the solid phase include polysaccharides (such as agarose and cellulose); and other mechanically stable matrices such as silica (e.g. controlled pore glass), poly(styrenedivinyl)benzene, polyacrylamide, ceramic particles and derivatives of any of the above. In preferred embodiments, the solid support comprises controlled pore beads retained in a column that are coated with the fixation agent.

Use of a solid support provides for not only the fixation of free thiols and amines in the biological solution but also the separation of different size S-nitrosothiols. Retaining larger proteins in a column allows for distinguishing between small molecular weight and larger molecular weight S-nitrosothiols. For example, small molecular weight S-nitrosothiols, such as S-nitrosocysteine, S-nitrosoglutathione and S-nitrosohomocysteine, contain only one nitrosylated thiol and no free thiols, and would therefore not be retained in a thiol capturing column, as described above. Further, larger molecular weight nitrosothiols such as S-nitrosoalbumin may in fact also contain a number of free thiols and would therefore be retained in the column. As such, methods described herein provide for determination of not only the total levels of S-nitrosothiols in a fluidized biological sample but also separation of different S-nitrosothiols having varied molecular weights that may have different biological significance relevant to a particular disease process.

The stability of S-nitrosothiols under physiological conditions is known to be dependent upon various factors including the nature of the thiol group (RS) to which the NO group is attached. Examples of RS molecules include glutathione, cysteine, albumin and hemoglobin. Other factors that affect the stability of S-nitrosothiols include pH, oxygen tension, redox state and the presence of trace amounts of transition metals. Thus, in the test methods, biological samples, also include additional components for controlling pH and/or complexing with trace metals in the sample.

The pH of the biological sample, during the assay method can be maintained at a pH that resists the breakdown of S-nitrosothiols or the precipitation of same. Accordingly, the pH is maintained in a near neutral range to prevent the instability of nitrosothiols that occurs under alkaline conditions or the precipitation of nitrosothiols that occurs under acidic conditions. Preferably, the pH is maintained in a range from about 6.5 to about 8.5.

Since S-nitrosothiol levels are affected in patients suffering a wide variety of diseases and conditions, the methods described herein may be useful in diagnosing these conditions, determining suitable treatment and monitoring the progression of disease and the effectiveness of treatment. Diseases and conditions in which nitrosothiol levels are affected include pulmonary disorders associated with hypoxemia and/or smooth muscle constriction in the lungs and airways and/or lung infection and/or lung inflammation and/or lung injury (e.g., pulmonary hypertension, ARDS, asthma, pneumonia, pulmonary fibrosis/interstitial lung diseases, cystic fibrosis, COPD); cardiovascular disease and heart disease (e.g., hypertension, ischemic coronary syndromes, atherosclerosis, heart failure, glaucoma); diseases characterized by angiogenesis (e.g., coronary artery disease); disorders where there is risk of thrombosis occurring; disorders where there is risk of restenosis occurring; inflammatory diseases (e.g., AIDS related dementia, inflammatory bowel disease (IBD), Crohn's disease, colitis, and psoriasis); functional bowel disorders (e.g., irritable bowel syndrome (IBS)); diseases where there is risk of apoptosis occurring (e.g., heart failure, atherosclerosis, degenerative neurologic disorders, arthritis, and liver injury (ischemic or alcoholic)); impotence; sleep apnea; diabetic wound healing; cutaneous infections; treatment of psoriasis; obesity caused by eating in response to craving for food; stroke; reperfusion injury (e.g., traumatic muscle injury in heart or lung or crush injury); disorders where preconditioning of heart or brain for NO protection against subsequent ischemic events is beneficial, central nervous system (CNS) disorders (e.g., anxiety, depression, psychosis, and schizophrenia); infections caused by bacteria (e.g., tuberculosis, C. difficile infections, among others), septic shock, renal disease, rheumatoid arthritis, diabetes, inflammatory joint diseases, cerebral ischaemia, preeclampsia, arteriosclerosis, brain injury, ocular injury and infection, and many others.

Other diseases and conditions in which nitrosothiol levels are affected include those diseases and conditions associated with ischemic tissue or tissue damaged by ischemia. In particular embodiments, the subject is a human who is has or who is at risk of having an ischemic tissue or tissue damaged by ischemia, e.g., a subject that has diabetes, peripheral vascular disease, thromboangiitis obliterans, vasculitis, cardiovascular disease, coronary artery disease or heart failure, or cerebrovascular disease, cardiovascular disease, or cerebrovascular disease.

Illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia, and thus, suitable for detection or monitoring of nitrosothiol levels using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

In addition, some drugs, such as the organic nitrates used in the treatment of angina, generate NO and may thereby affect S-nitrosothiol levels. Therefore, the methods described herein may also be useful in monitoring the efficacy of such therapies, particularly in cases of "nitrate tolerance." In addition, certain drugs under development, including nitrosylated nonsteroidal anti-inflammatory drugs (NSAIDs), contain a nitrosothiol group and the methods of described may be used in evaluating the metabolism and gastrointestinal toxicity of such drugs. Accordingly, in a further aspect, there is provided a method of diagnosing or monitoring in a patient the progress or treatment of a disease or condition in which S-nitrosothiol levels are affected, or of monitoring or evaluating the efficacy or toxicity of a drug therapy which affects S-nitrosothiol levels.

EXAMPLES

Example 1

We set out to adapt an analytically similar variance analysis to measure peptides in solution using a novel capacitive biosensor. Experimental conditions were designed for eventual application of the new device and signal processing strategy in a physiological context, defined by a relatively strong saline solution to match blood serum.

A capacitive biosensor functions on the principle of an altered dielectric at the electrodes surface to detect the presence of a biological molecule. In this approach, a ligand receptor is immobilized by binding to a polymer surface deposited at the tip of the electrode. Ligand binding to the surface receptor pushes the high dielectric water layer farther away and replaces it with the lower dielectric of the ligand, decreasing capacitance. Additionally, ligand binding can change the conformation of the polymeric layer, altering the capacitance further. This makes the immobilization technique important to the overall sensitivity of the sensor.

The capacitive biosensor can be modelled as three capacitors in series, the electrode surface, the biological layer and the electronic double layer capacitance. The capacitances add inversely so the total capacitance is dominated by the smallest capacitance in the series, ideally the capacitance of the biological layer. As the size of the electrode decreases, all these capacitances decrease accordingly, including the change in capacitance at the biological layer upon ligand biding. This creates a lower limit on electrode size possible that still provides adequate signal to noise fidelity. One possible way to overcome this limitation is an immobilization layer on the electrode that is also semiconductive. This would then be a capacitive sensor with field effect contributions, a hybrid between a purely capacitive and field-effect sensor. What signal is lost in detection surface area could be gained in field-effect. A semiconductive immobilization polymer that fulfills this criteria is polydopamine.

Dopamine contains a catechol and an amine group. In a basic environment it will form a polymer that is adherent to most surfaces. This polymer, polydopamine, has a quinone functional group that is a target for nucleophilic groups such as primary amines, forming a covalent bond with them. This makes polydopamine an idea immobilization polymer to bind antibodies to the electrode surface as any protein in solution will bind with the polydopamine layer. Additionally, dopamine belongs to a large family of molecules called melanins. Melanin films have been shown to form electronic-ionic hybrid conductors, similar to p-type semiconductors.

Coating an electrode with a polydopamine layer can make a capacitive sensor with a semiconductor-like tip that can be easily functionalized with a large variety of potential proteinaceous ligand receptors. We describe the use of an electrochemical approach to deposit polydopamine on the tip of a 5 μm carbon fiber electrodes. These electrodes are then further functionalized with a pituitary adenylate cyclase activating protein (PACAP) IgG antibody to sense PACAP ligand in solution. Upon ligand binding, resulting changes in the equivalent circuit are detected using a variance analysis methods adopted a software lock-in approach. The approach described here provides a simple and sensitive method for protein detection in solution. Sensitivities are dependent on the binding receptor, in this instance an IgG antibody, and are demonstrated here to provide adequate signal when presented with ligand in the nanomolar range. Finally, the general sensing strategy provided here holds promise for expansion to a large number of applications beyond immune-based sensing.

Experimental Section

Chemicals and Materials

Dopamine hydrochloride, pituitary adenylate cyclase activating protein (PACAP) and Met-Enkephalin acetate were purchased from Sigma-Aldrich (St. Louis, Mo.). Parylene insulated 5 μm carbon fiber electrodes were purchased from ALA Scientific (Farmingdale, N.Y.). Goat α-PACAP antibody was purchased from Santa Cruz Biotechnology (Dallas, Tex.). Sodium Phosphate, dibasic anhydrous ($Na_2HPO_4$) was used to make the 10 mM phosphate buffer. Tris base (Tris (hydroxymethyl) aminomethane) was used to make the 10 mM Tris buffer and Tris-buffered saline (TBS). All solutions were brought to the appropriate pH with HCl.

Voltammetric polydopamine deposition was performed using a Dagan ChemClamp headstage amplifier (Dagan, Minneapolis, Minn.). Data acquisition was performed using IGOR Pro (Wavemetrics, Lake Oswego, Oreg.) software controlling an ITC-1600 (Heka Elektronic, Bellmore, N.Y.) data acquisition system. Frequency response and sensing data was gathered using the same software and data acquisition system controlling a custom frequency-boosted VA-10X amplifier with capacitance compensation (NPI, Hauptstrasse, Germany).

Electrode Functionalization

Figure 5:
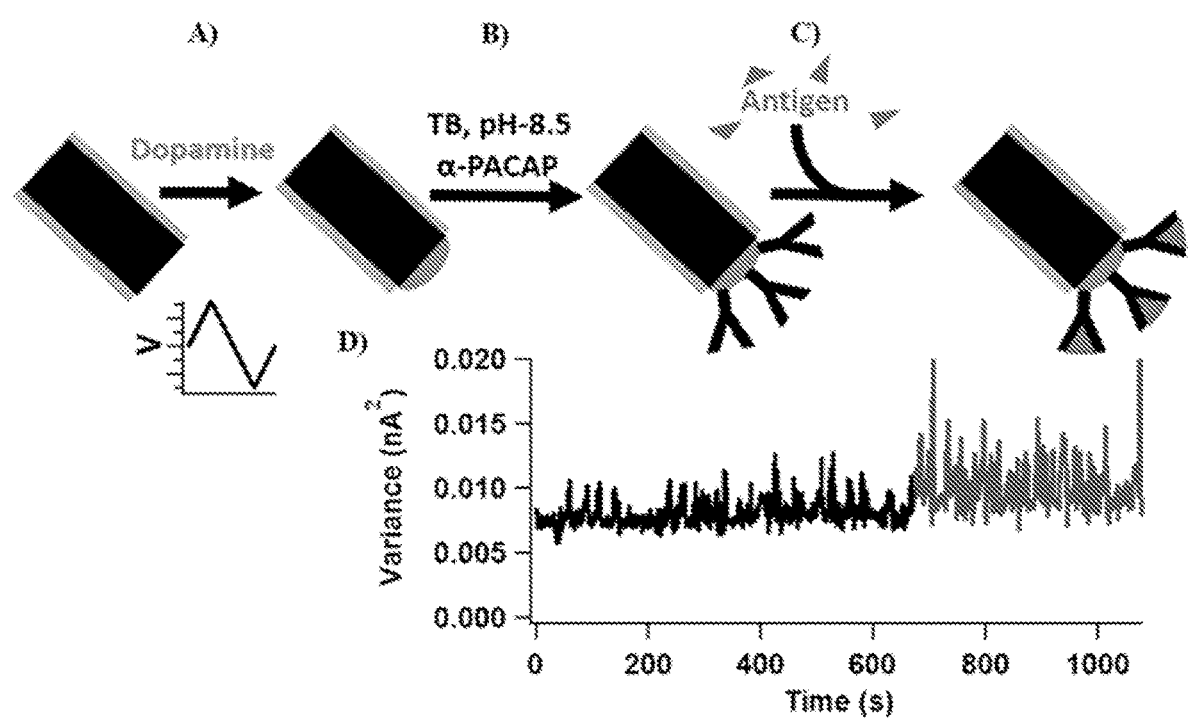
FIGS. 5(A-D) schematically illustrate sensor production and use. Cyclic voltammetry is used to deposit dopamine tip of a carbon fiber electrode (black rectangle) that is then incubated in a basics solution with a PACAP antibody. The functionalized antibody is then presented with PACAP and a change in signal variance is measured.

Polydopamine deposition was performed on a carbon fiber electrode with a freshly cut tip to expose a clean, conductive surface. Briefly, a sawtooth voltage waveform was applied between 650 mV and −600 mV at 20 mV/sec to an electrode superfused with 10 mM Phosphate buffer, pH-6.5 (FIG. 5A). The evoked current response is proportional to the amount of polydopamine deposited on the electrode and was sampled at 500 Hz and filtered through a 3 kHz, 3-pole Bessel low-pass filter. The current response during the first 5 cycles provided a baseline before superfusing with a phosphate buffer with 10 mM dopamine added. Polydopamine deposition was calculated after every voltage cycle as the cumulative charge and the deposition was stopped when the target charge was achieved.

Binding of PACAP IgG antibody was accomplished by mixing antibody (1 mg/mL) with 10 mM Tris buffer, pH-8.5 (FIG. 5B). The polydopamine coated electrode was tip-submerged in this solution and incubated in a 4° C. overnight.

Electrode Characterization

Frequency response was measured by applying a 10 mV sinusoid over a range of frequencies, with 10 to 50 msec gaps between each frequency transition. Each frequency was allowed to run between 32 and 78 cycles. The current response was sampled at 100 kHz and filtered through an 8 kHz, 2-pole Bessel low pass filter. This process was repeated and averaged 50 to 100 times while superfusing with Tris buffered biological saline (40 mM Tris base, 132 mM NaCl, 4.2 KCl, 11.2 Glucose, 2 $CaCl_2$, 0.7 $MgCl_2$, pH-7.25).

A software lock-in algorithm was used to determine the real and imaginary components of the evoked signal at each frequency. Equations 1 and 2 were used to calculate the real and imaginary components of the signal sinusoid. P is the total number of points in the averaged region. To avoid possible edge effects the first and last four cycles were not included in the average. The time and current at point p are $t_p$ and $I(p)$ respectively.

$$1)\ I_{Imaginary} = \frac{2}{p}\sum_{p=0}^{p-1} I(p) * \cos(\omega * t_p)$$

$$2)\ I_{Real} = \frac{2}{p}\sum_{p=0}^{p-1} I(p) * \sin(\omega * t_p)$$

The phase angle ($\omega$) is calculated by taking the inverse tangent of the ratio of the imaginary and real current.

$$\tan^{-1}(I_{Imaginary}/I_{Real}) \qquad 3)$$

Impedance components are calculated by dividing the current component by the applied voltage. Equation 4 was used to calculate the magnitude of the impedance.

$$|Z| = \sqrt{(Z_{Real}^2 + Z_{Imaginary}^2)} \qquad 4)$$

Sensing Experiments

Figure 4:
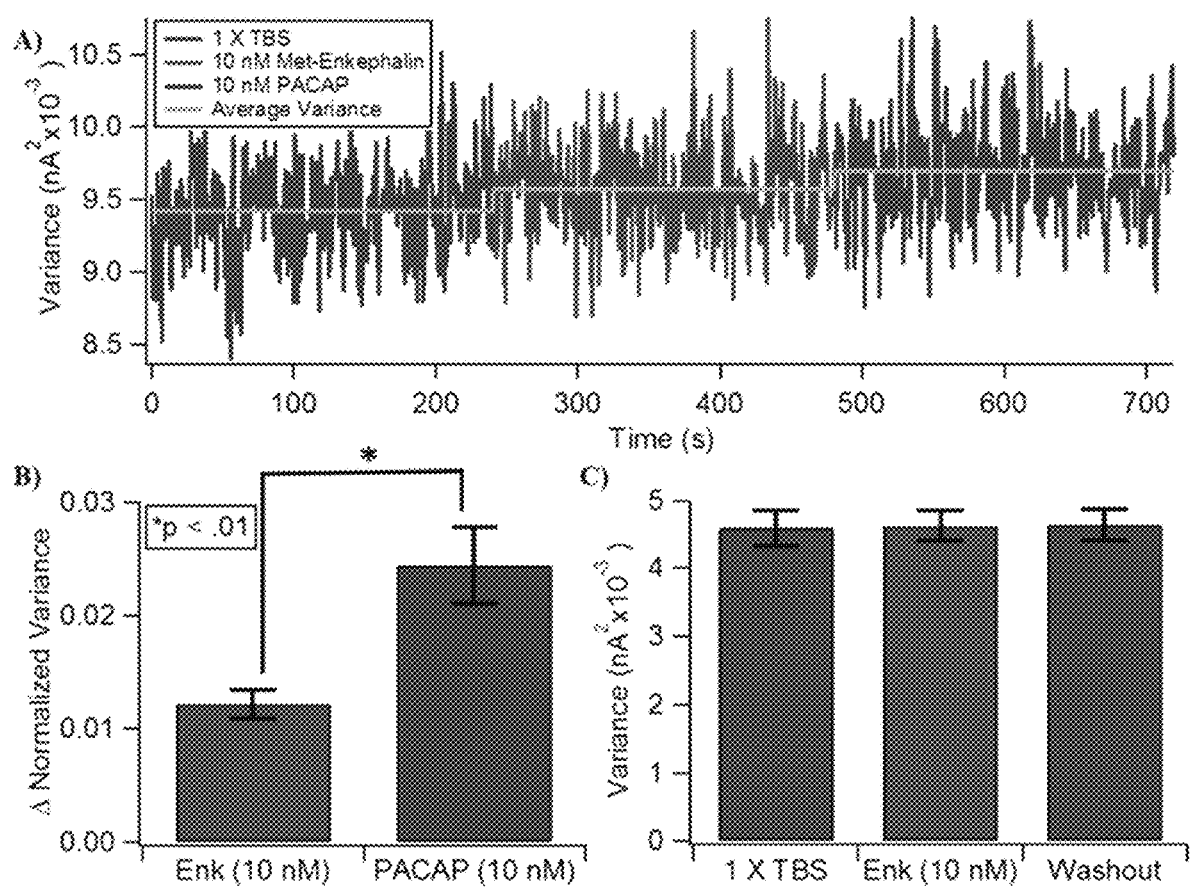
FIGS. 4(A-C) illustrate plots and graphs showing variance increases when functionalized electrodes are exposed to their antigen. (A) Variance response to baseline, 10 nM Met-Enkephalin, and 10 nM PACAP. (B) Variance difference between negative and positive controls (n=3). Normalized to variance while perfusing with TBS. Variance was measured during the last 2 minutes of perfusion. There was a significant difference between negative and positive controls (Student's t-test, p<0.01) Variance from a single electrode ran three times with 1XTBS, 10 nM Met-Enkephaline, and then TBS.

After characterizing the frequency response of each electrode, the frequency of the command potential sinusoid at which a particular electrode is most sensitive was determined. The electrode was driven with a 10 mV sinusoid at each electrodes characteristic frequency while superfusing with Tris buffered biological saline solution (FIG. 1C). The signal was sampled at 20 times the frequency of the command sinusoid and the lock-in algorithm was used to calculate average phase angle and amplitude over each sine cycle. Variance was calculated over every 1 second time period (FIG. 5D, FIG. 4A) and this variance was averaged over a two minute period at the end of a treatment condition for comparison between treatments (FIGS. 4 B, C).

Results and Discussion

Characterizing the Naïve Carbon Fiber Electrode

The frequency response of each naïve carbon fiber electrode had four characteristic impedance peaks (FIG. 1A). At 25 Hz, a high impedance is expected, and seen, as the electrode is designed to be predominantly capacitive. The next impedance peak is due to from a change in reactance, the imaginary component of the impedance, due to inductive and capacitive elements within the circuit. The peak nearest 500 Hz is due to a change in resistance. The highest frequency impedance peak is due to a change in reactance.

We chose the highest frequency impedance peak to analyze for ligand detection. This feature is dominated by the reactive component of the impedance (FIG. 1B) and a change in the reactance of the system is expected upon a change in the electrostatic environment at the electrode tip. Reactive elements, mainly capacitance, from the rest of the electrode should be minimal and constant due to the insulated coating of the electrode. Additionally, higher frequencies evoke a greater magnitude, which improves the signal-to-noise ratio.

The reactance appears discontinuous at the high frequency impedance peak (FIG. 1B). As the frequency increases to 1.2 kHz, a positive and increasing reactance was observed (FIG. 1B). A transition then occurs between 1.2 kHz and 1.225 k Hz where the phase and the reactance abruptly transitions to negative values. The large phase shift and increased impedance is characteristic of an anti-resonance, a region of destructive interference between oscillating elements of the circuit. The phase shift comes from moving from a positive reactance dominated region, typically attributed to an inductance, to a negative reactance dominated region associated with a capacitance.

The Anti-Resonance Feature is Sensitive to the Environment at the Electrode Tip

Figure 2:
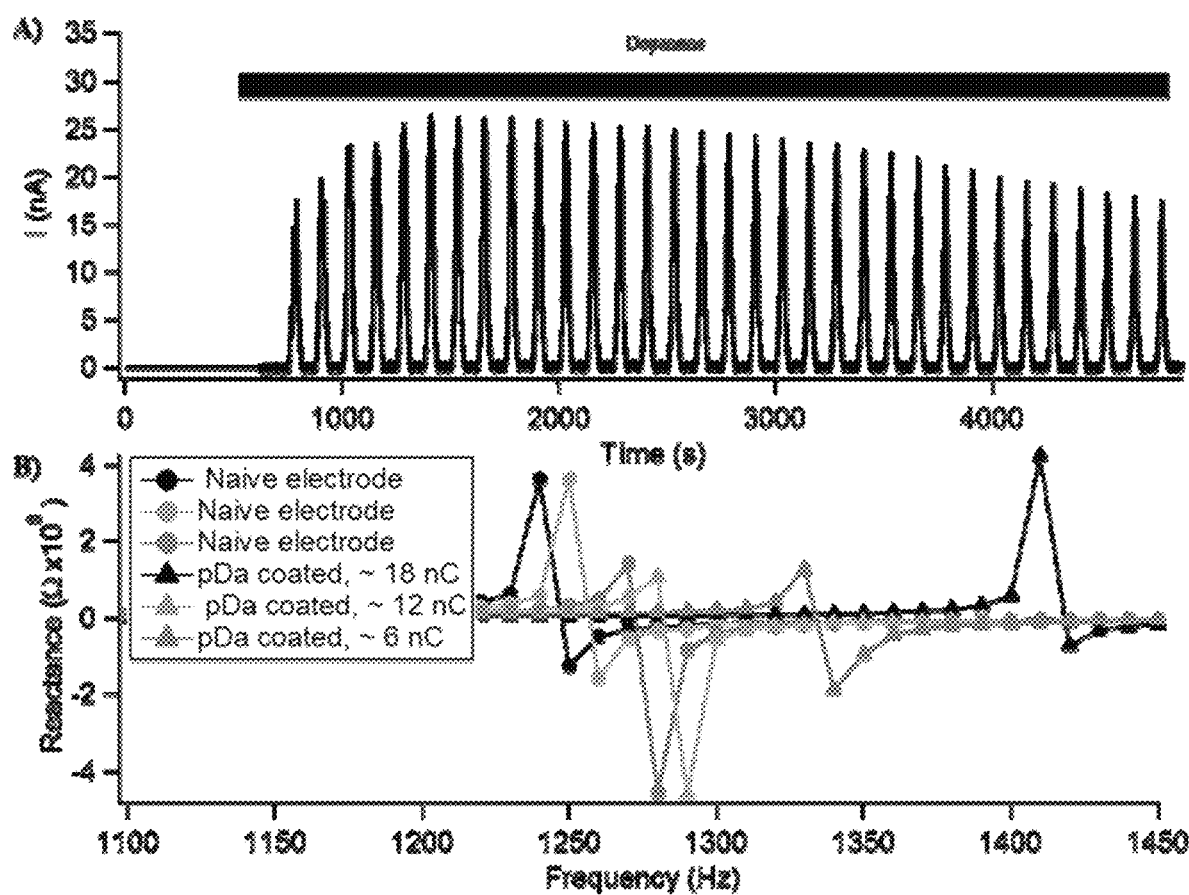
FIGS. 2(A-B) illustrate plots showing dopamine electrodeposition alters the anti-resonance frequency of the electrode. (A) Electrodeposition of polydopamine on the tip of a 5 μm carbon fiber electrode. Representative deposition curve showing the dopamine oxidation current. (B) Frequency response of three electrodes before (filled circles) and after (filled triangles) dopamine deposition, gathered from 1100-1450 Hz at 10 Hz increments and 78 cycles per frequency.

After characterizing the naïve electrode we adopted a protocol for polydopamine deposition at the electrode tip. We used integrated electrode current in response to a sawtooth command potential as an index of dopamine deposition. The deposition protocol included 5 cycles recorded in regular Tris buffer to provide a baseline. The solution was then changed to contain dopamine and resulted in an initial increase in recorded current for approximately 7 cycles, representing the wash-in of dopamine and oxidative polymerization of polydopamine on the conductive electrode tip. (FIG. 2A, 0-1500 s). During the eighth cycle the oxidative current began to decrease, consistent with a thickening coat of polydopamine on the carbon fiber tip (FIG. 2A, 1500 s to end).

Integration of the oxidative current is useful as a guide but should not be considered a quantitative measure of the amount of dopamine on the tip. A confounding effect emerges as polydopamine is deposited. A background subtraction method is used to determine oxidative current but this does not account for a change in the baseline reduction of buffer. Deposition of polydopamine on the tip will reduce the oxidation of dopamine but will also inhibit the reduction of phosphate to phosphine. This is the dominant current in the baseline and without it the baseline will shift more positive and give a falsely decreased integral. One possible solution to this is to switch to a constant potential dopamine deposition protocol.

The carbon fiber electrodes show inherent variability (FIG. 2B, Naïve electrodes). High frequency anti-resonance peaks have been seen, in the naïve electrodes, as low as 1100 Hz and as high as 1450 Hz. This variability is believed to be due to the cutting of the fiber before each deposition to provide a fresh surface (see Chemicals and Materials). Rinsing the cutting blades with ethanol before cutting and rinsing the electrode with ethanol after cutting appears to decrease this variability. The same electrode undergoing the same deposition protocol can exhibit different characteristics after re-cutting. This limitation requires normalization of signals to the variance under baseline conditions to allow for comparison.

Figure 3:
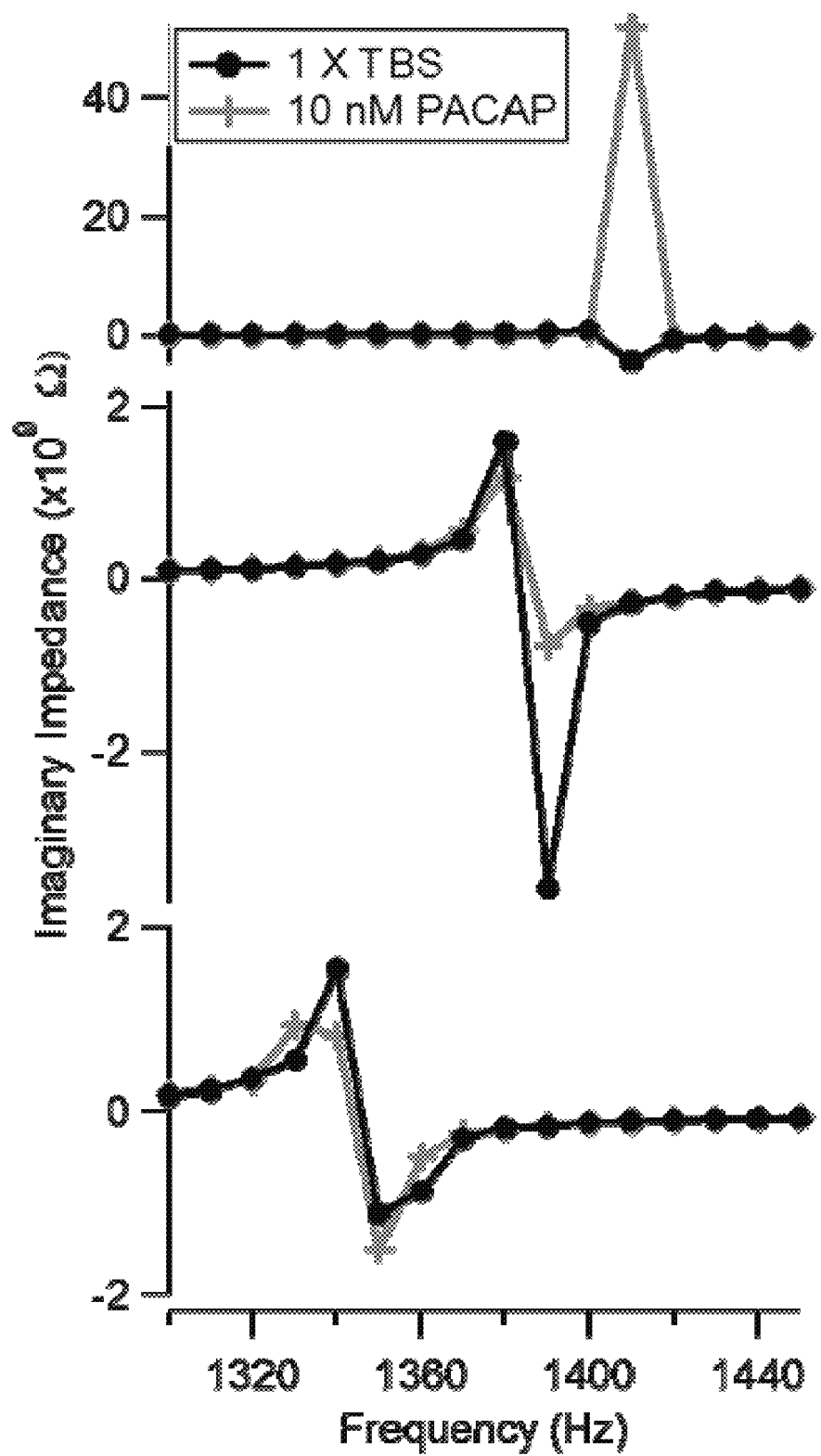
FIG. 3 illustrates plots showing anti-resonance-like peaks are altered in response to ligand treatment. Frequency response of three electrodes before and after 10 nM PACAP treatment, gathered from 1300-1450 Hz at 10 Hz increments and 78 cycles per frequency.

Dopamine deposition shifts the anti-resonance feature to a higher frequency (FIG. 2B). Three different total oxidative charges were considered with no correlation seen between the amount of charge and the frequency shift. One feature that did appear is an increase in cycle-to-cycle variance at the highest charge. The fiber with the greatest cumulative oxidative charge showed an increase in cycle-to-cycle variance while the two with a lesser cumulative oxidative charge showed a decrease (data not shown). If, as has been reported for melanin films, polydopamine has semiconductive properties, it would increase the cycle-to-cycle variance of the electrode due to an increase in the real part of the admittance. A semiconductive tip should increase sensitivity as you would no longer be measuring purely a change in capacitance upon ligand binding, but the resistance of the semiconductive tip would also be altered by field effects from any charge in the ligand. This could possibly lead to a change in the variance of the signal.

α-PACAP Functionalized Carbon Fiber Electrodes Show Increased Variance when Exposed to Ligand Initially, frequency response experiments were run to determine if the anti-resonance peak was shifted in response to ligand. The frequency response should be more sensitive due to the signal averaging and the ability to test over a range of frequencies. This approach is advantageous in that it provides a greater signal to noise ratio, but comes at the cost of temporal resolution. FIG. 3 shows the frequency response recorded in three separate α-PACAP functionalized electrodes. A change is seen in the anti-resonance frequency in response to PACAP presentation.

A trend towards a more robust response to PACAP is noted as frequency of the anti-resonance features, defined by the most negative value, increases (FIG. 3). The 1.41 kHz feature (FIG. 3, top) has a minimum of $-4.486 \times 10^9 \Omega$. With 10 nM PACAP in the bath, the maximum increases to $51.828 \times 10^9 \Omega$, representing a change of greater than an order of magnitude change. The 1.39 kHz feature (FIG. 3, middle) shifts upward by approximately $2.8 \times 10^9 \Omega$. Finally, the 1.35 kHz peak shifts downward less than $0.5 \times 10^9 \Omega$. It is unclear at this time if these results indicate a change in the shape of the anti-resonance feature, or a shift in the position of the feature. Based on this data, we only used electrodes with an anti-resonance feature at a frequency greater than 1.3 kHz.

FIG. 4A shows the variance of an α-PACAP functionalized sensor with a 1.35 kHz, 10 mV potential applied while perfusing with TBS, 10 nM Met-Enkephalin, and 10 nM PACAP, respectively. While a trend may appear, no significant increase in variance occurred during the Met-Enkephalin treatment (FIG. 4C) while a much larger, significant, increase in variance was measured with PACAP treatment (FIG. 4B). To control for variance increase due to non-specific interactions, a single electrode was run three times in succession with buffer, 10 nM Met-Enkephalin, and then buffer alone (FIG. 4C). Due to inherent differences in frequency response between electrodes we normalized to the variance during the ligand-free baseline. Sensors were perfused with TBS, 10 nM Met-Enkephalin, and then 10 nM PACAP. The change in the normalized variance from TBS is presented in FIG. 4B. The PACAP treatment doubled the signals variance over the negative control and this difference was significant ($p<0.01$).

We have demonstrated a capacitive immunosensor able to detect 10 nM PACAP in a physiological saline solution using variance analysis. A high frequency anti-resonance feature of the sensor's frequency response was identified that was sensitive to polydopamine coating at the tip. Attachment of a PACAP IgG antibody to the polydopamine layer allowed us to measure a change anti-resonance feature in response to PACAP presentation. We used this anti-resonance feature to determine a sinusoid frequency at which to do sensing experiments. A lock-in algorithm allowed us to measure a change in the signal variance in response to PACAP presentation at the sinusoid frequency in a biological saline solution.

We chose a frequency domain analysis, but it is theoretically possible to use the same sensor while applying a step potential. The current in response to the step function decays as the capacitor charges, this is measurement of an RC circuit. Changes in the capacitor, change the RC circuit, and thus the nature of the current decay. This has the disadvantage of having less time resolution, but in situations where time resolution is not required, it can be used.

Example 2

Impedimetric Antibody-Based Enkephalin Detection

FIGS. 7(A-C) illustrate a schematic representation of the impedimetric antibody-based detection technique. An electrode (carbon fiber or platinum) is functionalized by electrodeposition of polydopamine to which antibodies are covalently bound. Presentation with a non-specific ligand for the bound antibody does not result in tight binding and is ineffective at altering the capacitance formed and the electrode-solution interface. Presentation of the ligand to the bound antibody results in high affinity binding. This displaces high dielectric water and presents an immobile charged moiety to the tip of the electrode, altering the capacitance at the electrode-solution interface.

In this example, parylene-insulated carbon fiber electrodes were dipped into a TRIS-buffered saline with dopamine in solution. Step depolarizations were applied to the electrode to electrodeposit polydopamine onto the fiber tip. The electrode was then tip-dipped into a TRIS-buffered solution containing antibody for several hours. The electrode was then mounted to the input of a differential amplifier (1 channel for experimental and a second channel for a negative-control reference antibody expected to deliver no specific signal, GAPDH in this case) and exposed to a solution containing potential ligand. The equivalent circuit of the electrode was measured in a time-domain approach by stepping the electrode with alternating commands (Vc) to +10 and −10 mV. Resulting currents were recorded and digitized at 20 KHz and stored. Analysis consists of subtraction of the current measured through the reference electrode from the experimental electrode and measure of the resulting difference.

Figure 9:
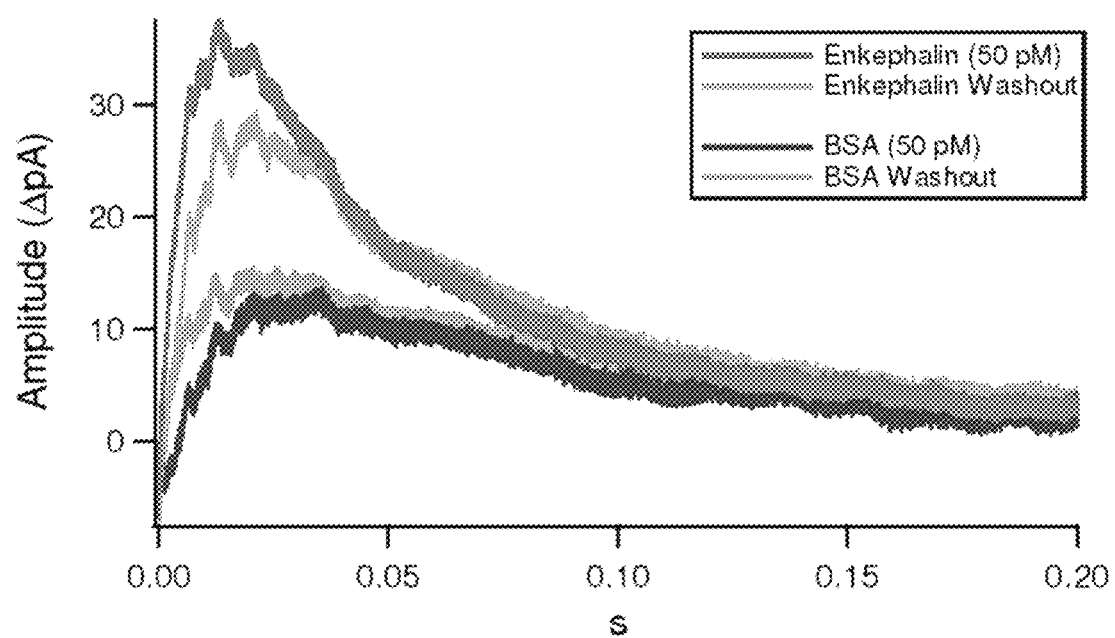
FIG. 9 illustrates plots showing example data obtained from an electrode bound with anti-enkephalin antibodies.

FIGS. 8(A-B) show that the capacitance at the electrode-solution interface was sampled by a step depolarization in the electrode-ground circuit (Vc=voltage command). The current injected into the circuit in response to the voltage step decays with kinetics defined by the RC (resistance and capacitance) of the circuit—a parameter altered by the antibody-ligand binding. Example data obtained from an electrode bound with anti-enkephalin antibodies shows increased signal amplitude in response to 50 pM enkephalin versus non-specific bovine serum albumin (BSA) (FIG. 9).

In Vitro Calibration of Enkephalin Detection

Two electrodes were prepared as described above; one with enkephalin antibodies and another with antibodies against Glyceraldehyde 3-phosphate dehydrogenase (GAPDH). Enkephalin serves as the positive condition and GAPDH as the negative control. Signal was measured in solution containing no (TRIS) or increasing concentrations of enkephalin. The measured current was normalized to the initial TRIS currents measured from each electrode. FIG. 10A shows Increasing concentrations of enkephalin increased the current measured in the enkephalin electrode (grey bars) but not the control GAPDH electrode (white bars). FIG. 10B shows currents measured in A are plotted against concentration in a semi-log plot and show that the currents follow typical pharmaco-kinetics.

Example 3

L-CSNO Sensor

We developed an S-nitroso-L-cysteine (L-CSNO) sensor in order to measure the presence and concentration of L-CSNO in blood. To accomplish this, we begin with insulated carbon fiber electrodes (ALA id CFE-2) and coated the tip with a thin layer of polydopamine. Before passivation, polydopamine is an electrophile and nucleophiles will covalently bond to it. We functionalized the sensor tip. We passivated the sensor tip in a solution of polyclonal rabbit anti-L-CSNO antibody in a solution of high pH (pH 8.2) Tris buffer. This ensures the sensor is coated with Tris and L-CSNO antibody. When L-CSNO binds to the antibody, it changes the local charge environment of the sensor's tip changing the signal. We then create a reference electrode by coating another insulated carbon fiber with polydopamine and passivating it with pure high pH Tris buffer.

Figure 11:
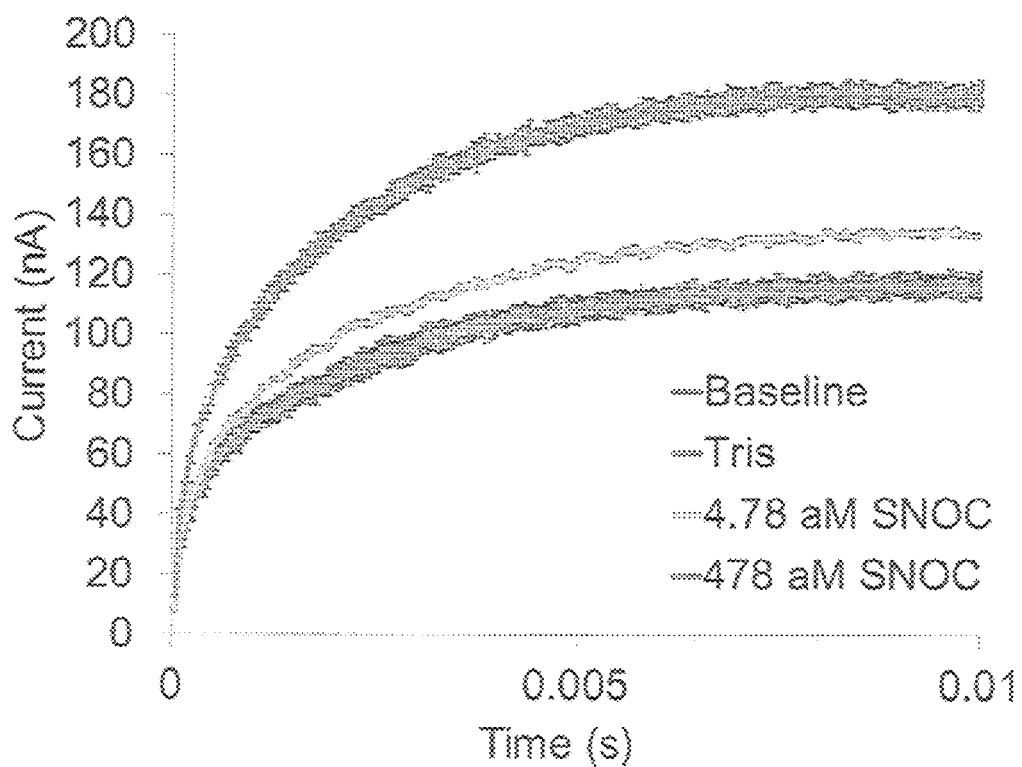
FIG. 11 illustrates a plot of the combined current versus time curve after the sensor was charged using either a positive or a negative current. This accentuates the asymmetry of the capacitance. The Baseline curve represents the sensor incubated in Tris buffered saline. The sensor was then infused with fresh buffer to produce the Tris curve. The sensor was then incubated in 4.78 aM SNOC for 10 minutes, washed with buffer and a reading was taken. Finally, the sensor was incubated with 478 aM SNOC for 10 minutes, washed with buffer and a reading was taken.

The bath was charged by applying a potential step to the Ag/AgCl pellet and the response to each electrode was recorded. The maximum response current from the sensing electrode is dependent upon the fraction of anti-L-CSNO antibodies binding L-CSNO. This sensor showed a significant change in maximum response in the presence of 4 pM L-CSNO and 40 µM SNO-Albumin and Albumin, but no significant change in response to other ligands similar to L-CSNO (SNO-Cysteamine, SNO-Glutathione, and L-Cysteine) (FIG. 11).

For each experiment, three sensing runs were conducted by charging the sensing and reference electrode with a 1 second, +50 mV direct current injection, and the allowing the electrodes to discharge for 1 second before charging the electrodes with a −50 mV direct current injection and again allowing them to discharge. The difference between the first 10 ms of the discharge current between when the probe was positively charged and negatively charged and this served as the signal for the sensor. We then collected three sensing experiments with the electrodes in 10 mM Tris buffered saline, pH 7.4 (Running Buffer) to serve as a baseline signal. We then perfused in 50 mL of Running Buffer and took an additional three readings to assess electrode stability. Finally, we incubated the sensing and reference electrodes in 10 mL of running buffer mixed with ligand or biological fluid and allowed it to incubate for 10 minutes. Afterwards the sensor was washed with 50 mL of Running Buffer and a final three experiments were performed to determine the signal we obtained from our solution.

Blood Assays Using the Probe

Venous blood was drawn from the antecubital fossa and arterial blood from the radial artery of normal, non-smoking, healthy volunteers on no medications. Blood was drawn into a heparinized syringe and immediately diluted 1:7 in Tris buffer (above). It was placed in a Petrie dish and analysed using the L-CSNO sensor relative to the reference electrode (see above). Phlebotomy was performed in accordance with an institutional review board protocol.

Figure 12:
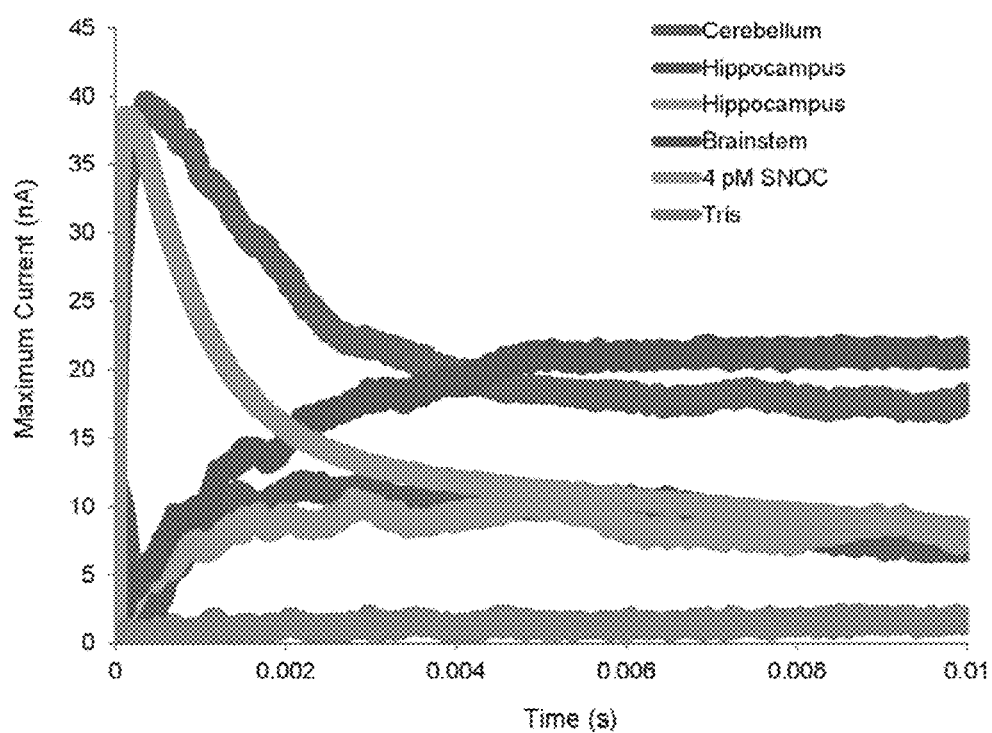
FIG. 12 illustrates a plot of the combined current versus time curve after the sensor was charged using either a positive or a negative current. This accentuates the asymmetry of the capacitance. The Baseline curve represents the sensor incubated in Tris buffered saline. The sensor was then infused with fresh buffer to produce the Tris curve. The sensor with incubated with SNOC or brain homogenate.
Figure 13:
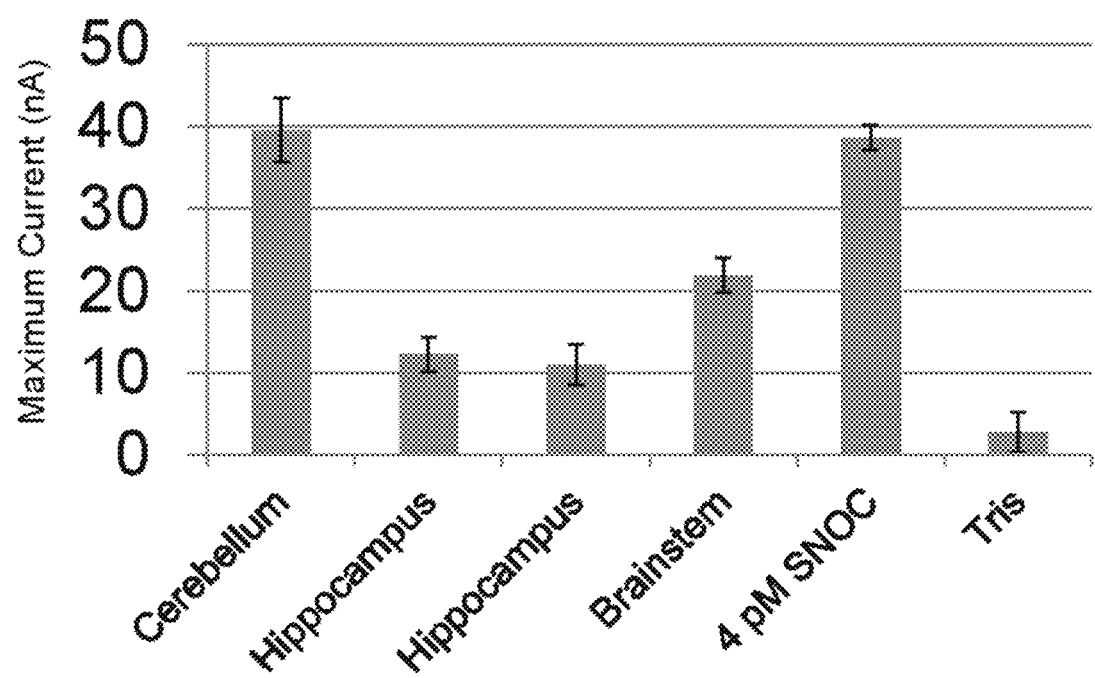
FIG. 13 illustrates a graph showing antibodies at the sensor's surface bound with ligand.

We extracted brains from male C57B6 mice and dissected those brains into their component parts. We then weighed and homogenized the brain tissue in 400 µl of 10 mM Tris buffered saline, pH 7.4 (Running Buffer), before further diluting the brain homogenate to 10 ml with running buffer. The sensing and reference electrodes were allowed to relax in pure running buffer and a baseline reading and two readings with fresh running buffer were taken to establish a stable baseline. Afterwards, the reference and sensing electrodes were incubated in the brain homogenate for 10 minutes before the sensor was cleaned with running buffer and a new reading was taken. The signal we are recording is marked by a fast rise in the charging of the sensing and reference electrode. This fast rise reaches its maximal amount in the first 10 milliseconds (FIG. 12). The maximal charging current experienced by the sensor is proportional to the percentage of antibodies at the sensor's surface bound with ligand (FIG. 13).

Example 4

This Example describes a method and technical specifications for building and running a SNO-specific capacitive biosensor. We show that our method detects minute quantities of SNOs, does not detect parent thiols in high concentration and does not give a signal in biological samples after application of methods, which specifically degrade SNOs. This sensor allows better detection of SNOs in a variety of biological systems.

Materials

Unless otherwise specified all reagents were obtained from Sigma-Aldrich. Carbon fiber electrodes were obtained from ALA Scientific (CFE-2). All buffers were made the day of the experiment in doubly deionized water. This is to prevent formaldehyde degradation in running buffer. All experiments were run in one of the following buffers. Plating Buffer: 10 mM Potassium Monobasic Phosphate Buffer adjusted to pH 7.5 using NaOH with 1 µMCuCl$_2$. The copper in solution enhances polydopamine's semiconducting properties. Running Buffer: 10 mM phosphate buffered saline, pH 7.4 with at least 0.8% formaldehyde. It is very important to use phosphate buffered saline that is low in metal contaminants, as copper and iron contamination will degrade SNOs and cannot be easily removed as most metal chelators are neutralized by formaldehyde. It is suggested to purchase low metal concentrated PBS to make running buffer.

Sample Preparation

Biological samples underwent centrifugation (30 sec at 14,000 rpm) to remove large aggregates and then separated using a 10 kDa spin filter (2 min at 12,000 rpm) to remove all large proteins and other particles. In particular, this would remove all SNO-degrading enzymes and all Cu binding proteins. There is no significant concentration of free Cu(II) in the blood serum we use for detection and hence no Cu-mediated degradation of SNOs is likely. The low mass fraction was collected, and two aliquots (100 µL each) were flash frozen with dry ice in ethanol. The first aliquot of 100 µL was diluted into 10 ml of running buffer and allowed to react at room temperature for 15 min. It was then run on the sensor. The second aliquot was incubated under a UV light and spiked with 3 mM HgCl$_2$ for 90 min to degrade all SNOs in solution. Afterwards, the sample was diluted into 10 ml of running buffer and incubated for 15 min before being run on the sensor. This negative control is essential to run with all biological samples to ensure there are no non-specific interactions with chemicals inside of the biological sample. If the negative control samples give a positive result, the concentration of formaldehyde in the running buffer should be increased to block all free amines and thiols.

Protocol

Figure 17:
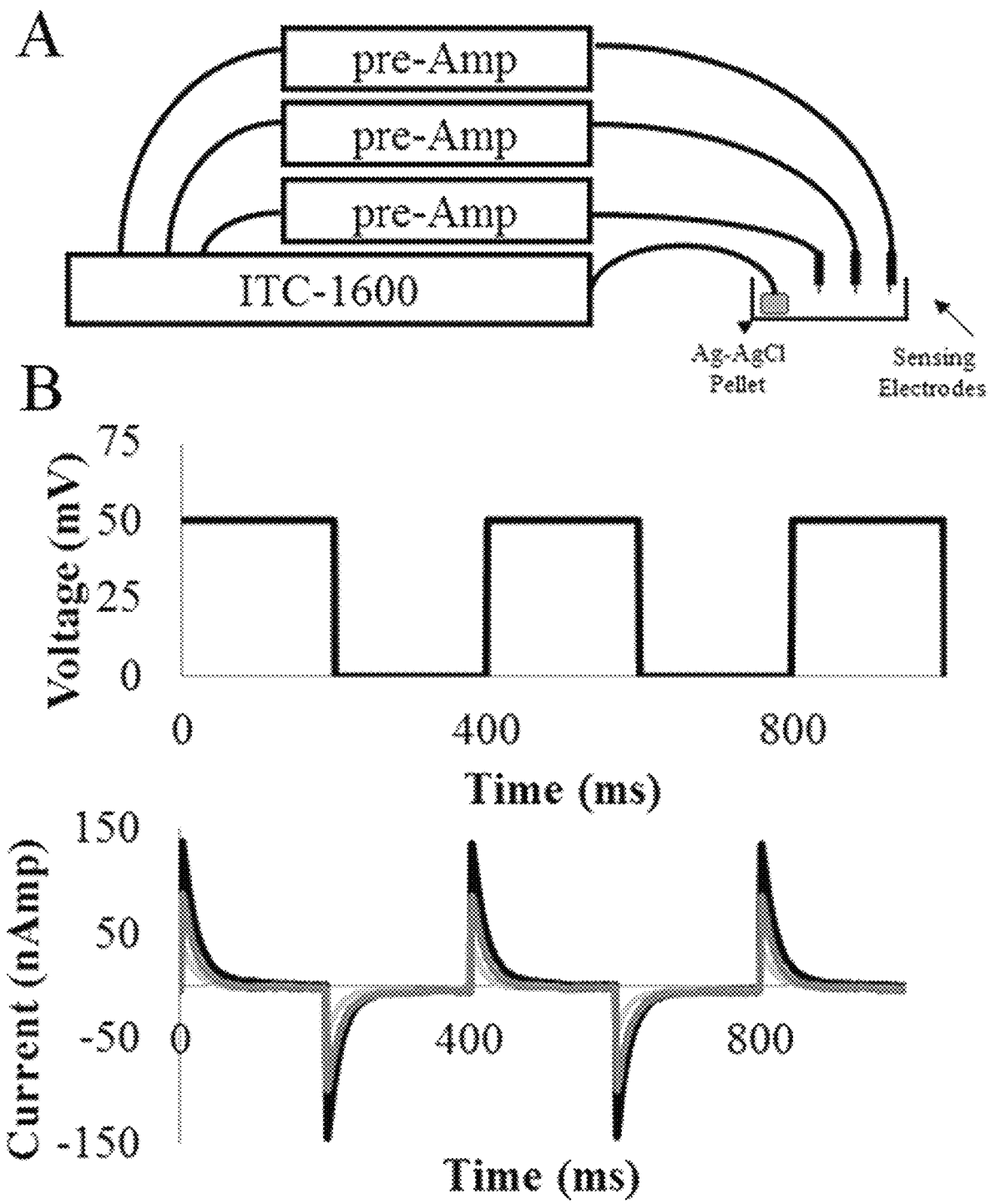
FIGS. 17(A-B) illustrate a schematic and example data of the sensing rig. (A) A schematic of the setup. (B) Example data trace showing the input voltage and the current response.

Up to 3 functionalized electrodes were attached to three separate pre-amplifiers (SR560, Stanford Research), which, in turn, were connected to three separate AD channels of an ITC-1600 (HEKA Corporation) (FIG. 17A). The entire setup was enclosed in a well ventilated Faraday cage to block out all ambient electrical noise. Current injection was provided by connecting a small Ag—AgCl ground pellet (E205, Warner Instruments) to a DC channel of the same ITC-1600. All pre-amplifiers were set to ground coupling and a 10× gain. The 3 electrodes were suspended above a 10 ml petri-dish such that the tips of the carbon electrodes would be submerged in running buffer when the petri-dish is filled. Once all 3 electrodes are positioned and attached to their pre-amplifiers and the ground pellet is placed in the petri-dish and connected to the ITC-1600, the petri-dish can be filled with running buffer and the circuit completed. Once the dish is filled, the pre-amplifiers should be set to DC coupling and the experiment can begin. It is very important that the pre-amplifiers must be set to ground coupling while the dish is filled so that current spikes caused by flowing saline near the electrodes before the circuit is fully formed do not damage the pre-amplifiers or the electrodes.

All experiments were performed at room temperature with no stirring of the solutions. Once all electrodes have their tips submerged in running buffer, the controls for the sensing experiment can begin. A single sensing experiment is conducted by applying a step potential across the electrodes using the following protocol. A step potential was applied across the electrodes by first stepping the potential to 0 mV, holding it for 200 ms and then stepping it up to 50 mV and holding it for 200 ms. This process was repeated for 30 sec or for a total of 75 repetitions of the step potential. The resulting current traces for all three electrodes via their preamplifiers were recorded simultaneously on three separate channels of a ICT-1600 data acquisition unit (FIG. 17B). A higher step potential can be used for electrodes that do not show a strong enough response to stimulation but a step potential of 150 mV or higher should never be used to avoid damaging the sensing electrodes. This represents a single recording during an experiment. A recording is taken before the experiment begins to ensure all electrodes are in good electrical contact with the running buffer. Then the system is perfused with 10 ml of running buffer and a Baseline recording is taken. The system is again perfused with 10 ml of running buffer to mimic a blank sample injection and a Blank Injection recording is taken. Afterwards the system is perfused with 10 ml of running buffer to mimic a washout step and a recording is taken. The raw data should be reviewed at this time to ensure there is no signal drift or other artifact in the data. If drift or artifact are observed, the data should be discarded and the Baseline, Blank Injection, and Blank Washout steps repeated until a stable baseline is obtained. Once the system is shown to have a stable baseline reading, the sample, prepared as described above, should be injected and allowed to incubate for 2 min before a Sample Injection recording is taken. The final injection volume is 100 µL of sample diluted into 10 ml of running buffer. Finally, after 4 min of total incubation time, the sample should be washed out of the petri-dish by injecting 20 ml of running buffer, and a final Sample Washout recording taken.

Immediately after the Sample Washout recording is taken, the electrodes should be removed from the petri-dish. The dish and its running buffer should be discarded and replaced with a fresh petri-dish. This is refilled as above to prepare for a new experiment. A single set of functionalized electrodes should not be used for sensing experiments more than 5 times in a row before being re-functionalized to prevent saturation of the polydopamine surface. Exposing electrodes to high concentrations (~nM to mM) of SNOs will saturate the electrodes after a single experiment, while samples without any SNOs will not saturate the electrodes at all. After electrodes have been removed from the old solution, the resulting data should be saved and processed as described below. The time that parylene coated electrodes sit in running buffer should be minimized as aqueous solution will slowly dissolve the parylene coating, creating pinholes in the insulating coating.

Absorption Spectroscopy

All absorption spectroscopy experiments were performed using a SpectraMax Plus 384 Plate Reader (Molecular Devices) with a standard 96 well plate (Costar, #3596). We mixed running buffer alone, 100 µM dopamine hydrochloride in running buffer, 100 µM 5-nitroso-L-cysteine (CSNO) in running buffer, and 100 µM dopamine hydrochloride and CSNO in running buffer and allowed all four samples to incubate for 15 min in the 96 well plate before a spectrum reading was taken between 350 nm and 750 nm in 5 nm increments.

Mass Spectrometry

All mass spectrometry was performed using a Thermo Finnigan LCQ Deca. We prepared 100 µM dopamine hydrochloride in running buffer, 100 µM CSNO in running buffer, and 100 µM dopamine hydrochloride and CSNO in running buffer and allowed all four samples to incubate for 15 min in Eppendorf tubes. Afterwards we directly infused 100 µL of each solution onto the mass spectrometer and recorded the resulting m/z range between 50 and 500 m/z for 18 s. The resulting mass spectra were averaged over the 18 s window and the averaged spectra were analyzed.

Statistical Analyses

All statistical analysis was done using Microsoft Excel 2016. To determine statistical significant differences from blank injections, we employed the Two Tailed Student's T-test, assuming a heteroscedastic distribution. Only differences with a p-value of less than 0.01 were considered to be significantly different from blank injections. All average normalized charge responses are presented with their mean value followed by the standard error.

Results

Interaction Between SNOs and Dopamine

Figure 18:
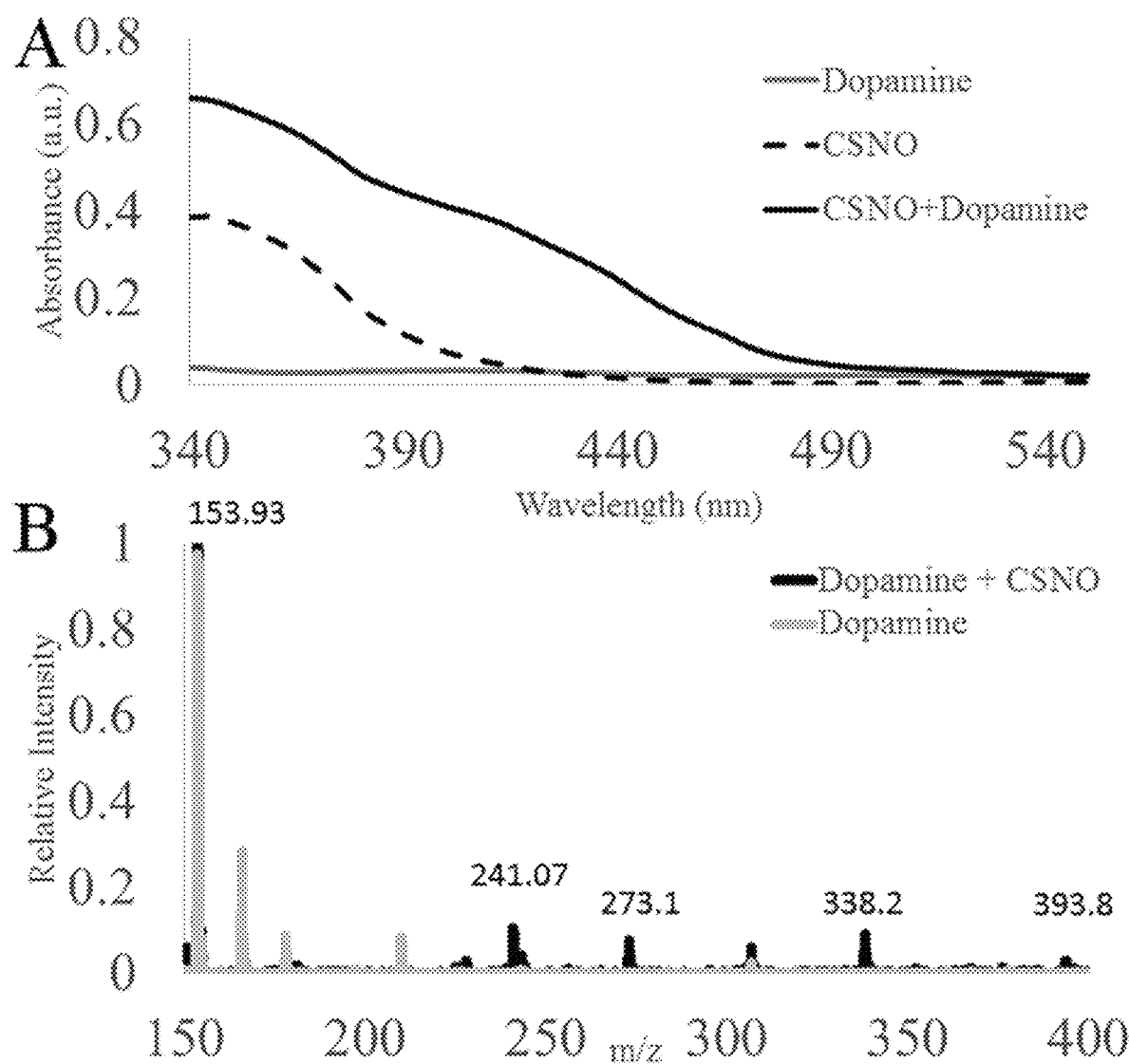
FIGS. 18(A-B) illustrate (A) the Absorption spectra of a dopamine, CSNO and dopamine+CSNO in running buffer. (B) Mass Spectra of either dopamine alone or CSNO with dopamine.

We measured the interaction between CSNO and dopamine by absorption spectrometry and mass spectrometry (FIG. 18). First we incubated 1 mM CSNO in running buffer for 15 min before adding equimolar dopamine for an additional 15 min. After that time, absorption spectra were taken of CSNO alone, dopamine alone, and CSNO+dopamine. Dopamine itself showed little absorbance between 340 and 550 nm, while CSNO showed a strong absorption around 340 nm. When mixed with dopamine, CSNO shows a stronger absorption at 340 nm, while gaining an absorption peak centered around 420 nm. This was further characterized by direct injection mass spectrometry. Here, we combined dopamine and CSNO in distilled water and incubated them for 15 min. We observed that this mixture formed di-sulfide cysteine or caused dopamine's mass to shift (FIG. 18B). The m/z peak 153.9 represents unreacted dopamine, 241 represents cystine, 273.1 represents dopamine covalently bound to 1 cysteine molecule, 338.2 represents dopamine covalently bound to 1 cysteine molecule and 1 formaldehyde molecule, 393.8 represents dopamine covalently bound to two cysteine molecules. All other peaks in this spectrum are contaminant peaks.

Dose Response for Limit of Detection

Figure 19:
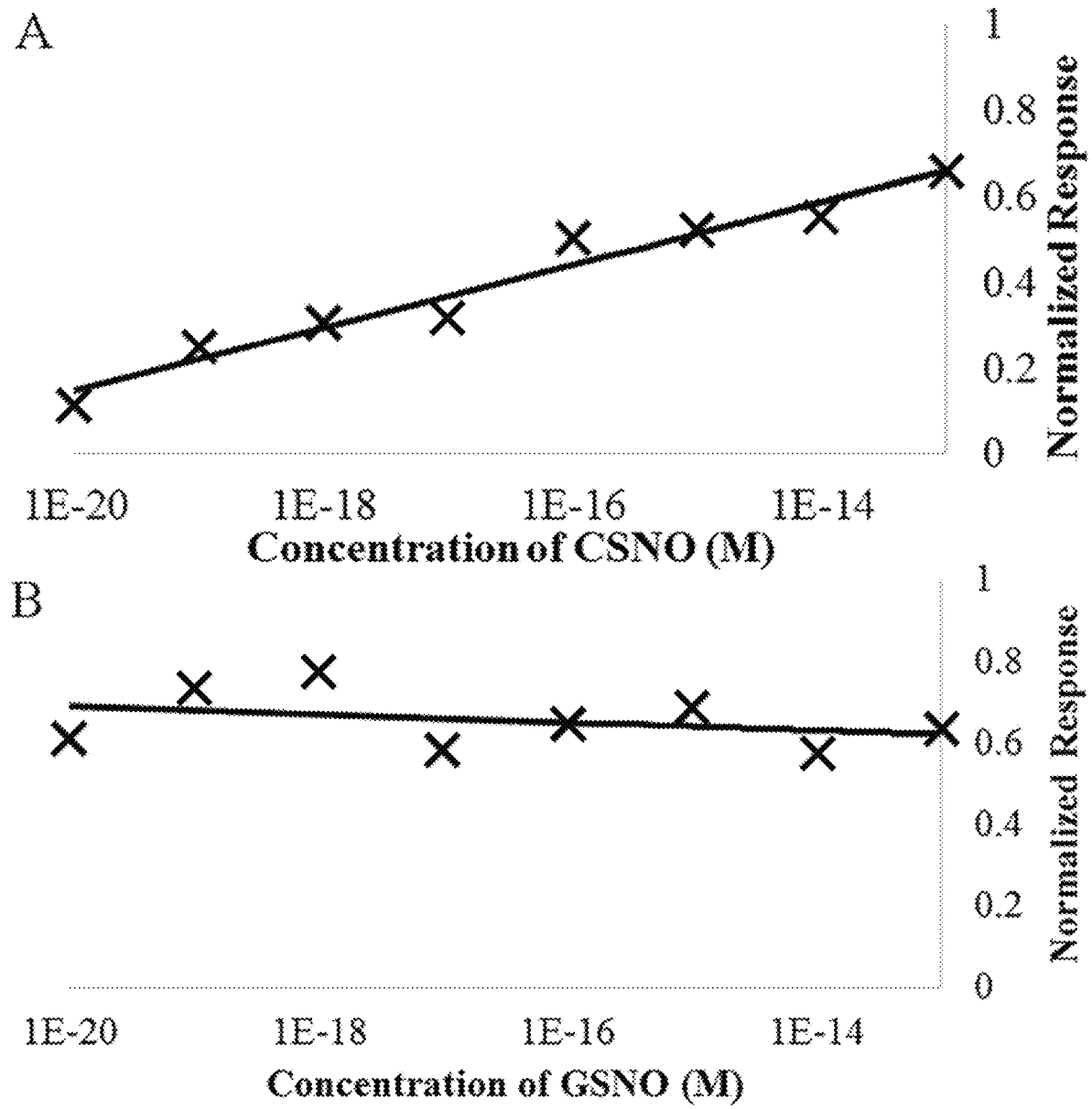
FIGS. 19(A-B) illustrate plots showing the average normalized response of the sensing electrodes after incubation with increasing concentrations of (A) CSNO, and (B) GSNO.

Functionalized sensing electrodes were tested for quality and then exposed to increasing concentrations of CSNO or S-nitroso-L-glutathione (GSNO) to test the relationship between small molecule SNO concentration and the normalized response of sensing electrodes to that compound (FIG. 19). This number is 0 for all times when the blank charge accumulation is larger, and ranges between 0 and 1 for times when the sample injection charge accumulation is larger. When running buffer in injected in place of a sample (Blank Injection), the electrode gives an average response of 0.030±0.065. Samples that contain a saturating concentration of SNOs, give an average response of 0.65±0.10. In general, individual electrodes have a high amount of variability with regards to the signal they produce, but a much more stable signal emerges when multiple electrodes are run in parallel and the results are average together.

By averaging the results of many separate sensing electrodes, we revealed a log-linear dependence between the concentration of CSNO and the normalized response (FIG. 19A). The correlation equation from fitting this data is r=0.0319 lnC+1.642 ($R^2$=0.9575), where r is the normalized response and C is the molar concentration of CSNO. The limit of detection (LOD) for CSNO is calculated to be $1.25 \times 10^{-19}$ M, or 0.125 aM. CSNO concentrations greater than 100 fM saturate the sensing electrode's response and do not produce a linear response with concentration. This is a marked improvement over published SNO sensors, which at best have a LOD of 50 nM. We also added increasing concentrations of GSNO to functionalized sensing electrodes and measured the response (FIG. 19B). We found that in contrast to CSNO, these sensing electrodes had no linear dependence with respect to concentration, and immediately saturate at a concentration of $1 \times 10^{-20}$ M, or 0.01 aM GSNO. Upon further investigation, the normalized response to GSNO jumps from 0.029±0.021 at $1 \times 10^{-21}$M GSNO to 0.612±0.083 at $1 \times 10^{-20}$M GSNO. This makes the effective LOD for GSNO $1 \times 10^{-20}$ M, or about 60 molecules of GSNO in 10 mL of running buffer. This means that the concentration of GSNO can be determine within a biological solution to within one log order by performing a serial dilution study to determine when the signal appears. It also means that it is possible to determine the difference between CSNO and GSNO in solution by seeing if the signal gradually fades with dilutions or suddenly vanishes.

The tepid response to CSNO compared to GSNO can also be partially explained by the relative stability of CSNO and GSNO in Running Buffer. We incubated 1 mM of either CSNO or GSNO in running buffer and monitored its stability by means of absorption at 340 nm. After 15 min of incubation in Running Buffer, only 59%±2% of CSNO added to the buffer remained in solution, while 90%±4% of GSNO added to the buffer remained. This degradation of CSNO and no GSNO is likely a combination of trace heavy metal contamination and pH degradation due to the relatively alkaline pH of our Running Buffer. SNOs that degrade during the incubation step will be blocked by the formaldehyde of the running buffer and hence will not interact with the sensing electrode. This most likely means that at ultralow concentrations of 1 zM, the sample fully degrades before interacting with the sensing electrode.

Specificity of Detection of SNOs

Figure 20:
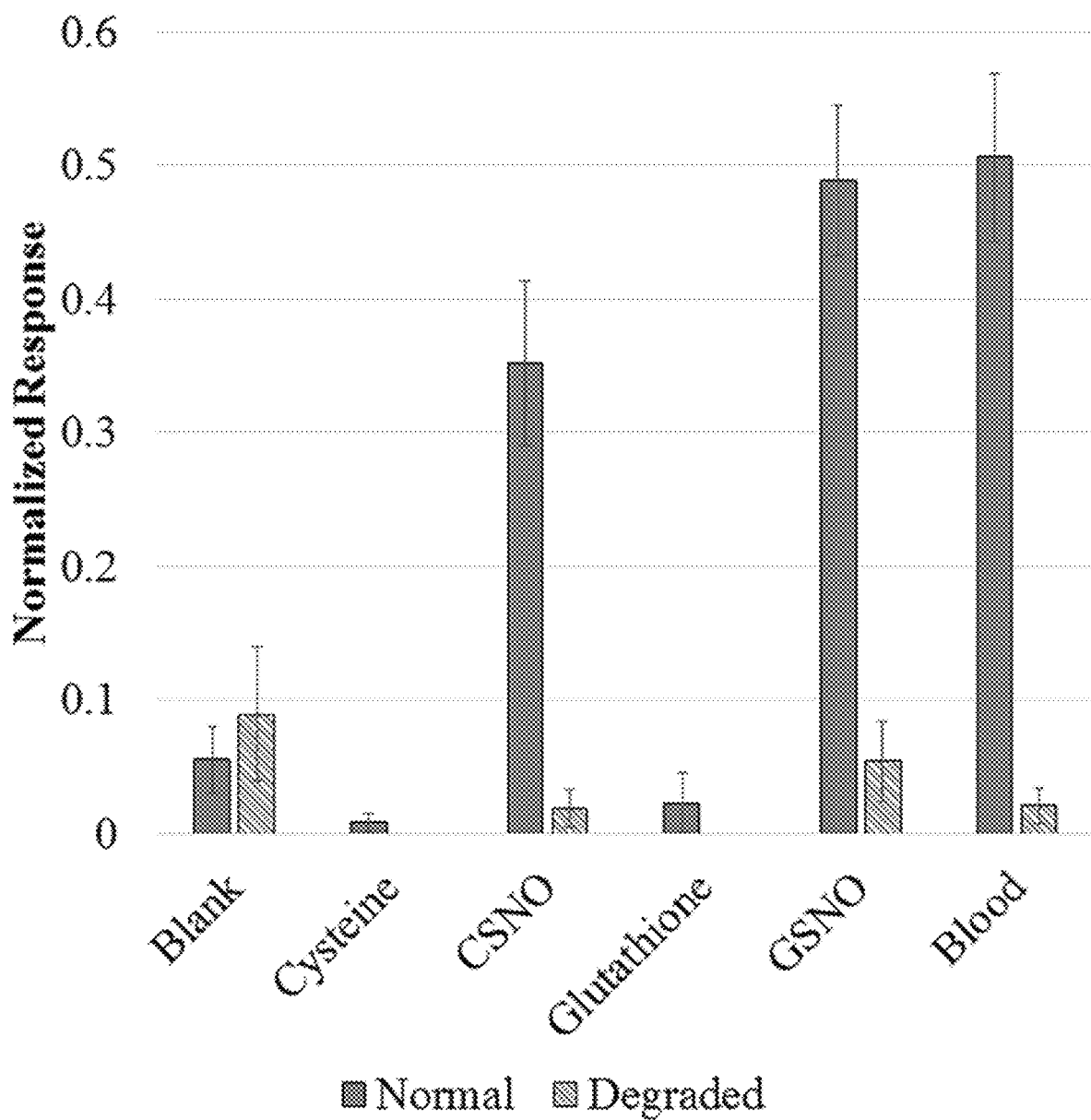
FIG. 20 illustrates a graph showing the average normalized response of the sensing electrodes after incubation with either: running buffer, 100 μM L-cysteine, 100 pM CSNO, 100 μM L-glutathione, 100 pM GSNO, or venous blood plasma. These samples were either prepared normally or preincubated with mercurous chloride and exposed to UV light to degrade all SNOs in solution.

We prepared samples of CSNO, GSNO, L-cysteine, L-glutathione and human venous plasma in the manner described in Sample Preparation, and ran each of these samples either: immediately or after pre-incubating them with of 3 mM HgCl and 90 min of exposure to UV light. UV light and HgCl are shown to degrade SNOs and as such should produce a negative signal. Solutions of CSNO and GSNO were prepared by diluting a stock solution of the SNO to 10 nM in distilled water and then mixing 100 μL of the stock with 10 ml of running buffer for a final, in petri-dish concentration of 100 pM SNO. The human plasma was prepared in an identical fashion to the stock SNO solutions. The resulting normalized response was recorded for each of these fluids (FIG. 20). Blank injections of 100 μL of distilled water and running buffer were also performed at the same time to ensure stability of the sensing electrodes. We prepared a 10 mM stock of cysteine or glutathione, and then injected 100 μL of the stock in 10 ml of running buffer for a final concentration of 100 μM. We did not prepare cysteine or glutathione under degrading conditions as neither has a potential S—NO bound to break. Of the samples prepared under non-degrading conditions only the CSNO, GSNO, and blood samples gave a significant (p<0.01) signal over that of a blank solution. Cysteine and glutathione samples showed no significant differences from blank buffer injections showing that while the sensing electrodes will react to trace concentrations of SNOs, they are insensitive to high concentrations of their parent thiols. No sample prepared under degrading conditions produces a signal significantly different from blank injections, strongly suggesting that the signal from the venous blood plasma was originally due to the presence of SNOs.

Sensitivity to Changes in Buffer

We injected blank running buffer at different pHs in place of real samples and recorded data both when the pH of the solution had shifted and then again once the pHed buffer had been washed out with 20 ml of normal running buffer. We calculated a response ratios and performed a Student's T-Test between all of the various pHs and blank buffers. We found that while alkalizing the running buffer does cause a slight false positive, it does not statistically significantly change (p<0.01) the response after the sample is washed out until the pH of the buffer is raised to 9.0 (FIG. 21A) This pH is destructive to S-nitrosothiols and would never be used in a laboratory setting. Acidifying the running buffer did not generate any false positives, but did affect the sensor by decreasing the inherent random drift that the sensor experiences, and hence slightly lowered the response. This was not statistically significant though with a pvalue of 0.17 for pH 5 washout and 0.75 for pH 5.5.

We mixed various concentrations of stock solutions of potassium, sodium or magnesium into running buffer normally and injected it in place of a real sample (FIG. 21B). Sodium gave no discernable signal, while potassium gave a significant (p<0.05) signal at 1M KCl. Magnesium did give a statistically significant false positive signal at concentrations of 5 mM $MgCl_2$ or higher. While this could pose a challenge to some experiments, the basal level of plasma magnesium levels has been reported to be 1 mM, much less than a level which would cause a significant false positive. Finally, should magnesium cause a false positive in lab tests, this can be resolved by simply further diluting the sample to ensure the injected sample has a concentration of magnesium lower than 5 mM. The relative insensitivity of the sensing electrodes to changes in ionic strength can be explained by the composition of the running buffer. As it is phosphate buffered saline, it already has a rather high ionic strength and hence small changes in the concentrations of ions, which would come from biological samples are unlikely to affect the real signal.

Biological Significance

The biological role of NO addition to heme groups in soluble guanylyl cyclase (sGC) and in hemoglobin is known. NO addition to protein thiols is now also known to be an important signaling reaction, termed S-nitrosylation, that is analogous to phosphorylation, glutathionylation, palmitoylation, acetylation and other physiological protein modifications. S-nitrosylation occurs downstream of cellular NO synthase (NOS) activity and through intermediate, endogenous low molecular weight SNOs (FIG. 22A). These latter, low molecular weight SNOs are endogenous, and the metabolism of each is regulated by specific enzymes. There are many examples demonstrating that this type of signaling occurs across a broad range of biological systems. Disorders of protein S-nitrosylation are relevant to the pathophysiology of many diseases, and S-nitrosylation is emerging as a field relevant to many biological disciplines. In addition, intermediate low molecular weight SNOs (FIG. 22A) appear to act as ligands in many signaling reactions. However, current assays for S-nitrosylated proteins lack sensitivity and often used near the limit of detection, which hampers research progress.

It should be emphasized that S-nitrosylation is as a regulated cellular process, rather than a non-specific toxicity. Many proteins catalyze the formation and degradation of protein SNO bonds. NOS activity can result in localized S-nitrosylation of co-scaffolded proteins, conventionally at cysteine S-nitrosylation motifs (FIG. 22A). Protein S-nitrosylation is also catalyzed by enzymes other than NOS. Note that protein denitrosylation is also enzymatically regulated; indeed, the kinetics of this denitrosylation can represent a major obstacle to accurate measurement in biological samples. However, a majority of protein S-nitrosylation-denitrosylation reactions appear to involve the formation of GSNO and other intermediate, low-mass SNOs. S-Nitrosylation reactions are involved in the full spectrum of cell signaling functions. They regulate epigenetic effects. S-Nitrosylation can regulate the expression of nuclear regulatory proteins, including NFκB, hypoxia-inducible factor (Hif) 1 and specificity proteins 1 and 2. S-nitrosylation affects the activity of membrane-associated proteins and degradation of many proteins.

There is emerging evidence that disorders of cellular processes described above are observed in a variety of pathophysiological processes ranging from cancer to Parkinson's disease. These disorders are major causes of morbidity, mortality and increased health care costs world-wide. The clinical translation of these findings has been severely hampered by the lack of a reliable, sensitive assay. We anticipate that this improved assay for GSNO has the capacity to transform management of diseases involving virtually every organ system. In many disease states, circulating or tissue levels of low mass-SNOs are abnormal. For example, they are low in severe, life-threatening asthma and high in life-threatening septic shock. The problem is that the limit of detection for these molecules using current technology is mid-nM. In many tissues, normal levels are at or near the limit of detection, and in disease states with increased catabolism, "low" often means "undetectable". There is universal agreement that a more sensitive assay is needed. It is clear that aM sensitivity of our capacitance method is more than needed but it certainly represents an important step forward in SNO-detecting technologies.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, we claim:

1. A capacitive sensor for the detection of an analyte in a fluid comprising:
    two or more sensing electrodes having a first and a second portion; the first portion of the sensing electrodes continuously covered with an insulator, the second portion of the sensing electrodes including an uninsulated electrode detection surface having a polydopamine semiconductive layer adhered to the electrode detection surface, wherein the second portion of the sensing electrodes is an exposed portion of the electrodes that define the electrode detection surface; and a receptor chemically functionalized to the polydopamine semiconductive layer of the electrode detection surface of the sensing electrodes, the polydopamine semiconductive layer or receptor selectively binding to the analyte of interest and the analyte once bound being detectable by measuring the change of capacitance of the sensing electrode;
    two or more reference electrodes having a polydopamine layer adhered to a reference electrode detection surface;
    a sensing chamber and a sample injection system, wherein the sensing chamber includes the two or more sensing electrodes and a voltage source, wherein the sensing chamber is a fluid filled chamber where fluid including an injected sample constantly flows from the sample injection system via a pump to a waste system, the sensing chamber providing a defined volume for sensing the presence and/or quantity of the analyte in the injected sample, and wherein the sample injection system includes the pump that supplies buffer to the sensing chamber and a sample injection loop for injecting the sample into the system;
    a metal shielding, wherein the metal shielding surrounds the sensing chamber, the two or more sensing electrodes, and the two or more reference electrodes; and
    a detection system, wherein the detection system includes two or more separate differential amplifiers that accept electrical signals from a single sensing electrode and reference electrode each and amplify the difference in current inputs between the single sensing electrode and reference electrode, and wherein the resulting amplified current is fed back to the voltage source and recorded.

2. The sensor of claim 1, wherein the two or more sensing electrodes comprise a carbon or platinum fiber.

3. The sensor of claim 1, wherein the receptor comprises at least one of an aptamer, oligomer, polymer, catalyst, cell, bacteria, virus, enzyme, protein, heptan, saccharide, lipid, glycogen, enzyme inhibitor, enzyme substrate, neurotransmitter, hormones, antigen, antibody, DNA, or RNA.

4. The sensor of claim 1, wherein presentation of a nonspecific ligand to the bound receptor is ineffective at altering the capacitance of the two or more sensing electrodes and presentation of a ligand for the receptor to the receptor results in binding of the ligand to the receptor and presents an immobile charged moiety to the surface active region of the sensing electrodes, altering the capacitance at the sensing electrode-fluid interface.

5. The sensor of claim 1, wherein the two or more sensing electrodes comprise a carbon fiber that is insulated to define the detection surface at a tip of the carbon fiber, the tip of the carbon fiber being covered with polydopamine.

6. The sensor of claim 1, being capable of quantifying an analyte in vivo when placed in a subject.

7. The sensor of claim 1, the receptor comprising an antibody or antigen binding fragment thereof.

8. The sensor of claim 7, wherein the antibody or antigen binding fragment binds enkephalin or S-nitroso-L-cysteine.

9. The sensor of claim 1, wherein the polydopamine semiconductive layer selectively binds directly to the analyte of interest and the analyte once directly bound being detectable by measuring the change of capacitance of the two or more sensing electrodes.

10. The sensor of claim 1, comprising three sensing electrodes, three reference electrodes, and three separate differential amplifiers.

11. The sensor of claim 1, wherein the voltage source includes a silver-chloride pellet.

12. The sensor of claim 1, wherein the resulting amplified current is recorded digitally.

13. The sensor of claim 1, wherein metal shielding shields the two or more sensing electrodes from electrical noise and provides an airtight chamber.

14. A capacitive sensor for the detection of an analyte in a fluid comprising:
- two or more sensing electrodes each having a first portion and a second portion, the first portions covered with an insulator, the second portions adhered to a polydopamine semiconductive layer that defines an exposed electrode detection surface of each of the sensing electrodes, and a receptor chemically functionalized to the polydopamine semiconductive layer of the detection surface of each of the sensing electrodes, the polydopamine semiconductive layer or receptor selectively binding to the analyte of interest and the analyte once bound being detectable by measuring the change of capacitance of the sensing electrode;
- two or more reference electrodes having a polydopamine layer adhered to a reference electrode detection surface;
- a sensing chamber and a sample injection system, wherein the sensing chamber includes the two or more sensing electrodes and a voltage source, wherein the sensing chamber is a fluid filled chamber where fluid including an injected sample constantly flows from the sample injection system via the pump to a waste system, the sensing chamber providing a defined volume for sensing the presence and/or quantity of the analyte in the injected sample, and wherein the sample injection system includes a pump that supplies buffer to the sensing chamber and a sample injection loop for injecting the sample into the system;
- a metal shielding, wherein the metal shielding surrounds the sensing chamber, the two or more sensing electrodes, and the two or more reference electrodes; and
- a detection system, wherein the detection system includes two or more separate differential amplifiers that accept electrical signals from a single sensing electrode and reference electrode each and amplify the difference in current inputs between the single sensing electrode and reference electrode, and wherein the resulting amplified current is fed back to the voltage source and recorded.

15. The sensor of claim 14, wherein the two or more sensing electrodes comprise a carbon fiber with a tip, the tip defining the detection surface of the electrode.

16. The sensor of claim 14, wherein the polydopamine semiconductive layer selectively binds directly to the analyte of interest and the analyte once directly bound being detectable by measuring the change of capacitance of the two or more sensing electrodes.

17. The sensor of claim 14, comprising three sensing electrodes, three reference electrodes, and three separate differential amplifiers.

18. The sensor of claim 14, wherein the voltage source includes a silver-chloride pellet.

19. The sensor of claim 14, wherein the resulting amplified current is recorded digitally.

20. The sensor of claim 14, wherein metal shielding shields the two or more sensing electrodes from electrical noise and provides an airtight chamber.

* * * * *